US008133974B2

(12) United States Patent
Zon et al.

(10) Patent No.: US 8,133,974 B2
(45) Date of Patent: Mar. 13, 2012

(54) FERROPORTIN1 NUCLEIC ACIDS, PROTEINS, ANTIBODIES AND METHODS

(75) Inventors: Leonard I. Zon, Wellesley, MA (US); Adriana Donovan, West Roxbury, MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

(21) Appl. No.: 12/381,770

(22) Filed: Mar. 16, 2009

(65) Prior Publication Data
US 2010/0048862 A1 Feb. 25, 2010

Related U.S. Application Data

(60) Continuation of application No. 11/641,589, filed on Dec. 19, 2006, now Pat. No. 7,521,055, which is a division of application No. 09/715,927, filed on Nov. 17, 2000, now Pat. No. 7,166,448, which is a continuation-in-part of application No. 09/567,672, filed on May 9, 2000, now abandoned.

(60) Provisional application No. 60/133,382, filed on May 10, 1999.

(51) Int. Cl.
C07K 14/00 (2006.01)

(52) U.S. Cl. ...................................................... 530/350

(58) Field of Classification Search .................. None
See application file for complete search history.

(56) References Cited

U.S. PATENT DOCUMENTS

| | | | | |
|---|---|---|---|---|
| 6,420,526 | B1 * | 7/2002 | Ruben et al. | 530/350 |
| 6,762,293 | B2 | 7/2004 | van Duijn et al. | |
| 7,166,448 | B1 | 1/2007 | Zon et al. | |
| 7,521,055 | B2 | 4/2009 | Zon et al. | |
| 2007/0218055 | A1 | 9/2007 | Zon et al. | |

OTHER PUBLICATIONS

Bisson, et al, 1993, Crit Rev Biochem Mol Biol, 28:259-308.*
Liang, H., et al (1998) Mol. Cell. Biol. 18(2): 926-933.*
Donovan, A., et al.; GenBank No. 7109244; Accession No. AF226612; *Danio rerio* ferroportin1 (fpn1) mRNA, complete coding sequence; Release Date: Feb. 29, 2000.
Donovan, A., et al.; GenBank No. 7109246; Accession No. AF22613; *Mus musculus* ferroportin1 (Fpn1) mRNA, complete coding sequence; Release Date: Feb. 29, 2000.
Donovan, A., et al.; GenBank No. 7109248; Accession No. AF22614; *Homo sapiens* ferroportin1 (FPN1) mRNA, complete coding sequence; Release date: Feb. 29, 2000.
McKie, A.T., et al.; GenBank No. 7657099; Accession No. NM._014585; *Homo sapiens* ferroportin1; iron regulated gene 1 (FPN1), mRNA; Release date: Mar. 20, 2000.
Fujiwara, T., et al.; GenBank No. 966878; Accession No. D63209; HUM506F01B Clontech human placenta polyA+ mRNA (#6572) *Homo sapiens* cDNA clone GEN-506F01 5', mRNA sequence; Release Date: Aug. 29, 1995.
Marra, M., et al.; GenBank No. 2235263; Accession No. AA500296; vi97h02.r1 Barstead mouse pooled organs MPLRB4 *Mus musculus* cDNA clone Image:920211 5', mRNA sequence; Release Date: Jul. 1, 1997.
Hillier, L., et al.; GenBank No. 1300295; Accession No. W23461; zb33c01.r1 Soarse parathyroid tumor NbHPA *Homo sapiens* cDNA clone Image:305376 5', mRNA sequence; Release Date: May 6, 1996.
Hillier, L., et al.; GenBank No. 1278239; Accession No. W05488; za84h11.r1 Soares fetal lung NbHL19W *Homo sapiens* cDNA Image:299301 5', mRNA sequence; Release Date: Apr. 23, 1996.
Kaplan, J., et al., "Mining the genome for iron," *Nature* 403:711-713 (2000).
Richardson, D.R., "Another jigsaw piece towards solving the iron metabolism puzzle: the cloning of the iron exporter, *ferroportin1,*" *Redox Report* 5(1):7-9 (2000).
Griffiths, W. and Cox, T., "Haemochromatosis: novel gene discovery and the molecular pathophysiology of iron metabolism," *Hum. Mol. Genet.* 9(16):2377-2382 (2000).
Donovan, A., et al., "Positional cloning of zebrafish *ferroportin1* identifies a conserved vertebrate iron exporter," *Nature* 403:776-781 (2000).
McKie, A.T., et al., "A Novel Duodenal Iron-Regulated Transporter, IREG1, Implicated in the Basolateral Transfer of Iron to the Circulation," *Mol. Cell* 5:299-309 (2000).
Abboud, S. and Haile, D.J. "A Novel Mammalian Iron-regulated Protein Involved in Intracellular Iron Metabolism," *J. Biol. Chem.* 275:19906-19912 (2000).
Montosi, G., et al., "Autosomal-dominant hemochromatosis is associated with a mutation in the ferroportin (*SLC11A3*) gene," *J. Clin. Invest.* 108(4):619-623 (2001).
Njajou, O.T., et al., "A mutation in *SLC11A3* is associated with autosomal dominant hemochromatosis," *Nature Genetics* 28:213-214 (2001).
GenBank accession No. NM._014585; *Homo sapiens* solute carrier family 40 (iron-regulated transporter), member 1 (SLC40A1), mRNA sequence; Release Date: Jun. 9, 2003.

(Continued)

*Primary Examiner* — Gary Nickol
*Assistant Examiner* — Sandra Wegert
(74) *Attorney, Agent, or Firm* — Hamilton, Brook, Smith & Reynolds, P.C.

(57) ABSTRACT

Positional cloning has been carried out to identify the gene responsible for the hypochromic anemia of the zebrafish mutant weissherbst. The gene, ferroportin1, encodes a novel multiple-transmembrane domain protein, expressed in the yolk sac. Zebrafish ferroportin1 is required for the transport of iron from maternally-derived yolk stores to the circulation, and functions as an iron exporter when expressed in *Xenopus* oocytes. Human and mouse homologs of the ferroportin1 gene have been identified. The invention includes isolated polynucleotides, vectors and host cells comprising nucleotide sequences encoding Ferroportin1 proteins and variants thereof, including those having iron transport function. The invention also includes polypeptides encoded by ferroportin1 genes and variants of such polypeptides, and fusion polypeptides comprising a Ferroportin1 or a portion thereof. Methods to produce a Ferroportin1, methods to produce antibodies to a Ferroportin1 and methods to identify agents binding to a Ferroportin1, which can be inhibitors or enhancers of Ferroportin1 iron transport activity, are also described. Inhibitors of Ferroportin1 activity can be used in a therapy for hemochromatosis.

1 Claim, 4 Drawing Sheets

OTHER PUBLICATIONS

Fleming, R. E. and Sly, W. S., "Ferroportin mutation in autosomal dominant hemochromatosis: loss of function, gain in understanding," *J. Clin. Invest. 108*(4): 521-522 (2001).
Bisson, L.F. and Coons, D.M., "Yeast Sugar Transporters," *Crit. Rev. Biochem. Mol. Biol*, 28(4):259-308 (1993).
Liang, H., et al., "Trinucleotide Insertions, Deletions, and Point Mutations in Glucose Transporters Confer K+ Uptake in *Saccharomyces cerevisiae*," *Mol. Cell. Biol. 18*(2):926-935 (1998).
Dodsworth, S.J., et al., GenBank No. 1028149, Accession No. Z56918; *H. sapiens* CpG island DNA genomic Mse1 fragment, clone 15368, forward read cpg15368.ft1a; Release Date: Oct. 19, 1995.
Arden, K.E., et al., "A Novel Mutation in Ferroportin1 is Associated with Haemochromatosis in a Solomon Islands Patient," *Gut 52*:1215-1217 (2003).
Shastry, B.S., "SNP Alleles in Human Disease and Evolution," *J. Hum. Genet. 47*:561-566 (2002).
Jun. 21, 2006, Amendment, U.S. Appl. No. 09/715,927.*
Dec. 8, 2005, Amendment, U.S. Appl. No. 09/715,927.*
Jan. 12, 2005, Amendment and Interview Summary, U.S. Appl. No. 09/715,927.*
May 11, 2004, Amendment and Interview Summary, U.S. Appl. No. 09/715,927.*
Jul. 25, 2003, Amendment, U.S. Appl. No. 09/715,927.*
Dec. 31, 2002, Amendment, U.S. Appl. No. 09/715,927.*
May 14, 2002, Preliminary Amendment and Reply to Restriction Requirement, U.S. Appl. No. 09/715,927.*
Mar. 21, 2006, Office Action, U.S. Appl. No. 09/715,927.*
Sep. 17, 2004, Office Action, U.S. Appl. No. 09/715,927.*
Nov. 23, 2003, Office Action, U.S. Appl. No. 09/715,927.*
Apr. 21, 2003, Final Office Action, U.S. Appl. No. 09/715,927.*
Jul. 31, 2002, Office Action, U.S. Appl. No. 09/715,927.*
Jan. 14, 2002, Office Action, U.S. Appl. No. 09/715,927.*
Dec. 11, 2008, Notice of Allowance and Examiner's Amendment, U.S. Appl. No. 11/641,589.*

* cited by examiner

```
Zebrafish FPN1  M D S P A S K K P R - - C E R F R E F K S A K F L I Y V G H A L S T W G D R   37
Human     FPN1  M T R A G D H N R Q E R G C C G S L A D Y L T S A K F L L Y L G H S L S T W G D R   40
Mouse     FPN1  M T K A R D Q T H Q E G C C G S L A N Y L T S A K F L L Y L G H S L S T W G D R   40

Zebrafish FPN1  M W N F A V A V F L V E L Y G N S L L L T A V Y G L V V A G S V L L L G A I I G    77
Human     FPN1  M W H F A V S V F L V E L Y G N S L L L T A V Y G L V V A G S V L V L G A I I G    80
Mouse     FPN1  M W H F A V S V F L V E L Y G N S L L L T A V Y G L V V A G S V L V L G A I I G    80

Zebrafish FPN1  D W V D K N P R L K V A Q T S L V V Q N S A V I L C G A L L M A V F Q F K Q Q L   117
Human     FPN1  D W V D K N A R L K V A Q T S L V V Q Q N V S V I L C G I H L M L V F L H K H E L   120
Mouse     FPN1  D W V D K N A R L K V A Q T S L V V Q Q N V S V I L C G I H L M V F L H K N E L    120

Zebrafish FPN1  S S M Y D G W L L T T C Y I M V I S I A N I A N L A S T A M S I T I Q R D W V V   157
Human     FPN1  L T M Y H G W V L T T S C Y I L H I T H I A N L A S T A T A I T I Q R D W I V    160
Mouse     FPN1  L T M Y H G W V L T T V C Y I L H I T H I A N L A S T A T A I T I Q R D W I V    160

Zebrafish FPN1  V V A G D D R S K L A D M N A T V R I I D Q L T N I L A P M L V G Q I M A F G S   197
Human     FPN1  V V A G E D R S K L A N M N A T I R R R I D Q L T N I L A P M A V G Q I M T F G S   200
Mouse     FPN1  V V A G E N R S R L A D M N A T I R R R I D Q L T N I L A P M A V G Q I M T F G S   200

Zebrafish FPN1  H F I G C G F I S G W N L F S M C L E Y F L L L W K V Y Q K T P A L A F K A G Q K   237
Human     FPN1  P V I G C G F I S G W N L V S M C V E Y V V L L W K V Y Y Q K T P A L A V K A G L K   240
Mouse     FPN1  P V I G C G F I S G W N L V S M C V E Y F L L W K V Y F L L W K V Y Q K T P A L A V K A A L K   240

Zebrafish FPN1  D S D D Q E L K H L N I Q K E I G N T E S P V E A S Q L M T E S S - - - - E   271
Human     FPN1  E - - E T E L K Q L N L H K D T E P K - - P L E G T H L M G V K D S N I H E L E   277
Mouse     FPN1  E - - E S E L K Q L T S P K D T E P K - - P L E G T H L M G E K D S N I R E L E   277

Zebrafish FPN1  P K K D T G C Y Q M A E P H R T F K D G W V A Y Y N Q S I F F A G M S L A F L    311
Human     FPN1  H E Q E P T C A S Q M A E P F R T F R D G W V S Y Y N Q P V F L A G M G L A F L   317
Mouse     FPN1  C E Q E P T C A S Q M A E P F R T F R D G W V S Y Y N Q P V F L A G M G L A F L   317
```

FERROPORTIN1 NUCLEIC ACIDS, PROTEINS, ANTIBODIES AND METHODS

RELATED APPLICATIONS

This application is a continuation of U.S. application Ser. No. 11/641,589, filed on Dec. 19, 2006, now U.S. Pat. No. 7,521,055, which is a divisional of U.S. application Ser. No. 09/715,927, filed Nov. 17, 2000, now U.S. Pat. No. 7,166,448, which is a continuation-in-part of U.S. application Ser. No. 09/567,672, filed May 9, 2000, now abandoned, which claims the benefit of U.S. Provisional Application No. 60/133,382, filed on May 10, 1999. The entire teachings of the above applications are incorporated herein by reference.

GOVERNMENT SUPPORT

The invention was supported, in whole or in part, by a grant R01 DL53298-02 from the National Institutes for Health. The Government has certain rights in the invention.

BACKGROUND OF THE INVENTION

Defects in iron absorption and utilization lead to iron deficiency and overload disorders. Adult mammals absorb iron through the duodenum, whereas embryos obtain iron through placental transport. Iron uptake from the intestinal lumen through the apical surface of polarized duodenal enterocytes is mediated by the divalent metal transporter, DMT1 (Fleming, M. D., et al., *Nature Genet.*, 16:383-386, 1997; Gunshin, H., et al., *Nature*, 388:482-488, 1997; Andrews, N. C., N. *Engl. J. Med.*, 341:1986-1995, 1999). A second transporter has been postulated to export iron across the basolateral surface to the circulation. The function of this iron transporting protein may be perturbed in mammalian disorders of iron deficiency or overload. Drugs to alter the function of this iron transporting protein may be useful to treat such diseases as hemochromatosis and some forms of anemia.

SUMMARY OF THE INVENTION

The invention relates to a number of nucleic acids, wherein the nucleic acids have SEQ ID NO:1, 3, 5 or 7 as described herein or the nucleic acids have nucleotide sequences related to those given specifically by SEQ ID NO by properties of hybridization, or by varying extents of identity, or by varying degrees of similarity as can be determined by a computer program designed for the purpose of comparing nucleotide or amino acid sequences. SEQ ID NO:1 is the nucleotide sequence of a cDNA encoding a zebrafish ferroportin1; SEQ ID NO:3 is the nucleotide sequence of a cDNA encoding a mouse ferroportin1; SEQ ID NO:5 is the nucleotide sequence of a cDNA encoding a human ferroportin1. SEQ ID NO:7 is the nucleotide sequence of a genomic DNA comprising the introns and exons of a human ferroportin1 gene. Also part of the invention are contiguous portions of any of the above nucleic acids, nucleic acids encoding any of the amino acid sequences described herein and nucleic acids encoding polypeptides which are variants of the Ferroportin1 proteins described herein by amino acid sequence. Further nucleic acids which are part of the invention are those encoding a fusion polypeptide comprising a Ferroportin1 or a portion of a Ferroportin1.

Related to the isolated nucleic acids are vectors and host cells comprising nucleotide sequences identical to the isolated nucleic acids of the invention. In some cases, regulatory sequences can be operably linked to coding regions to allow expression of a gene. Such cells can be maintained under conditions in which the gene is expressed and the encoded polypeptide is produced. The polypeptide can be purified by one or more steps to increase the proportion of polypeptide in the milieu of medium and material of cellular origin, thereby producing isolated polypeptide.

The term regulatory element refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals and enhancers, for instance.

The invention also includes Ferroportin1 proteins, for example, those having amino acid sequence SEQ ID NO:2, SEQ ID NO:4 or SEQ ID NO:6, proteins which are naturally occurring mutants or variants of those proteins characterized by those specific amino acid sequences, and mutants and variants of those proteins identified as having the specific amino acid sequence SEQ ID NO:2, 4, or 6 that are produced by laboratory manipulations of the nucleic acids encoding a Ferroportin1. Also within the invention are contiguous portions of any of the polypeptides with SEQ ID NO:2, 4, or 6, or portions of such mutants or variants of the polypeptides described herein as containing amino acid substitutions, or described herein as having a certain percent identity or similarity to another sequence in a comparison. A further embodiment of the invention is a fusion polypeptide, which can comprise a Ferroportin1 of full-length amino acid sequence, as in SEQ ID NO:2, SEQ ID NO:4 or SEQ ID NO:6, or a contiguous portion thereof, or can comprise any of the mutants or variant polypeptides, or portions thereof, as described herein, for example by their amino acid sequence identity or similarity to an amino acid sequence identified by SEQ ID NO, or by their activity (e.g., iron transport function) or property of binding to antibodies produced by immunizing an animal with a Ferroportin1.

Antibodies that bind to one or more Ferroportin1 proteins are also an aspect of the invention. Antibodies to a Ferroportin1 of one or more species can be produced, for example, by introducing into an animal which is not the source of the Ferroportin1 immunogen a Ferroportin1 or an immunogenic portion thereof in a suitable medium, which can include such substances as stabilizing agents and adjuvant. Other known methods can be used to make hybridomas producing monoclonal antibodies that bind to one or more Ferroportin1 proteins, as isolated, or as they exist in a cell membrane.

Other aspects of the invention include methods for identifying agents which bind to a Ferroportin1 (or to a mutant, variant, Ferroportin1 fusion protein or a contiguous portion of any of the foregoing) by steps that include contacting the agent with the isolated protein under conditions appropriate for binding of the agent to the isolated protein, and detecting a resulting agent-protein complex. Similar methods can be used to identify an agent which is an inhibitor or an enhancer of a function of a Ferroportin1 protein, where the steps can be the following: (a) combining (1) said isolated protein; (2) the ligand of said protein; and (3) a candidate agent to be assessed for its ability to inhibit interaction between said protein of (1) and the ligand of (2), under conditions appropriate for interaction between the said protein of (1) and the ligand of (2); (b) determining the extent to which said protein of (1) and the ligand of (2) interact; and (c) comparing the extent determined in (b) with the extent to which interaction of said protein of (1) and the ligand of (2) occurs in the absence of the candidate agent to be assessed and under the same conditions appropriate for interaction of said protein of (1) with the ligand of (2); wherein if the extent to which interaction of said protein of (1) and the ligand of (2) occurs is less in the presence of the candidate agent than in the absence of the candidate agent, the candidate agent is an agent which inhibits interaction between said protein and the ligand of said protein. If greater export of the iron from the test cells compared to export of the iron from the control cells is observed, this is indicative that the agent is an enhancer of iron export by said protein. An agent can be further tested for its effect on a Ferroportin1 protein in an animal, if the following steps are carried out: a) administering the agent to one or more test animals; b) measuring exogenously supplied iron in one or more samples of tissue or bodily fluid from said test animals; c) measuring exogenously supplied iron in one or more comparable samples of tissue or bodily fluid from suitable control animals; and d) comparing the iron of b) with the iron of c); whereby, lower iron in step b) than in step c) is indicative that the agent is an inhibitor of said protein. An inhibitor of the iron transport function of a human Ferroportin1 can be used in a method for treating hemochromatosis in a human, said method comprising administering to the human an inhibitor of Ferroportin1 iron transport function, or such inhibitor can be used in a method for treating a disease or medical disorder resulting from oxidative damage in a mammal, said method comprising administering to the mammal an inhibitor of Ferroportin1 iron transport function. Enhancers of a Ferroportin1 can be used in a method for treating iron deficiency anemia in a mammal, said method comprising administering to the mammal an enhancer of Ferroportin1 iron transport function.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2A-2B is an amino acid sequence alignment of zebrafish (SEQ ID NO:2), human (SEQ ID NO:6) and mouse (SEQ ID NO:4) Ferroportin1 (FPN1). The initiator methionine in all three species was established by the presence of upstream, in-frame stop codons. Shading indicates identical amino acids. Bars under sequence indicate predicted transmembrane domains. The mutations identified in the weh$^{tp85c}$ and weh$^{th238}$ alleles are indicated by black circles below the affected amino acids.

DETAILED DESCRIPTION OF THE INVENTION

Figure 1:
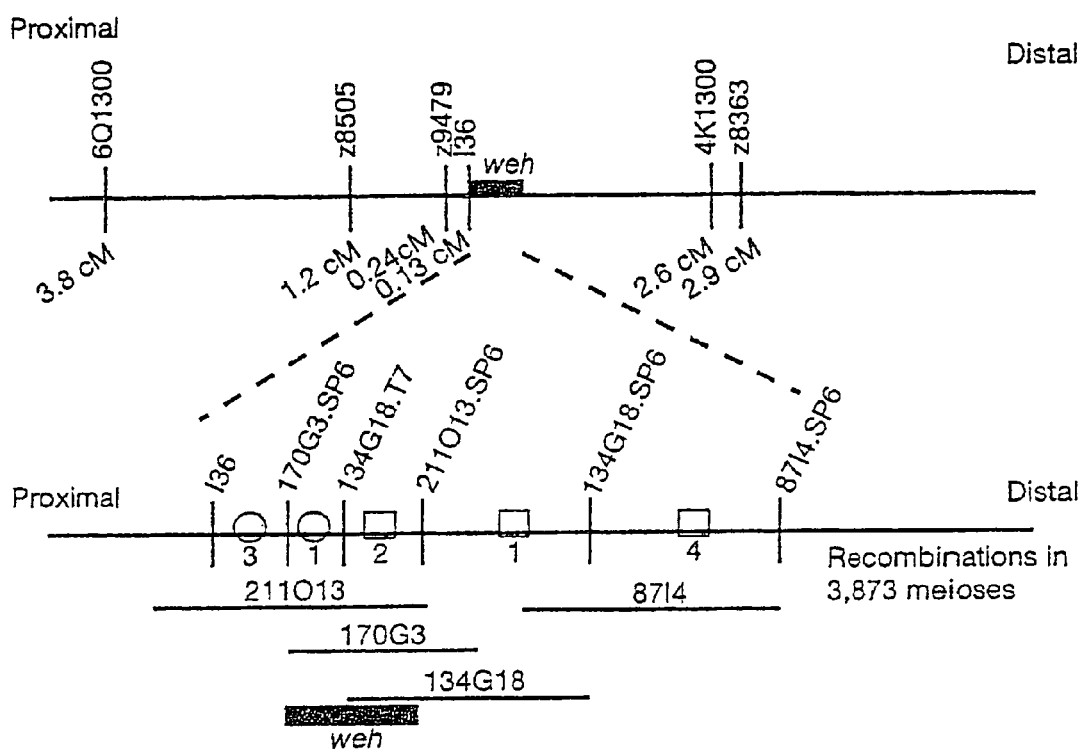
FIG. 1 is a map of the weh locus showing positional cloning of the weissherbst gene. The weh locus is depicted by a thick black bar just distal to the AFLP marker 136. Below the map is an enlarged view of the weh locus that depicts the BAC and PAC genomic clones identified by a chomosomal walk in an analysis of 3873 meioses. Genotyping of a total of 1783 meioses from haploid animals and 2090 meioses from diploid mutants narrowed the critical interval containing the gene to the PAC clones 211O13 and 170G3. The numbers of recombination events identified on the proximal side (circles) and distal side (squares) of the weh locus are indicated.

A description of example embodiments of the invention follows.

Iron is required for many cellular processes, but it can also be toxic when present in excess. Thus, iron homeostasis must be strictly maintained. Studies described herein employed zebrafish genetics to identify the multiple-transmembrane domain protein Ferroportin1, an iron export protein. In the mammalian yolk sac and placenta, Ferroportin1 may play an important conserved role in the transport of iron from the maternal to the embryonic circulation. In adults, Ferroportin1 is likely to function in iron transport at the basolateral surface of duodenal enterocytes. In disorders such as iron deficiency or overload, tissues respond by altering normal iron utilization. Ferroportin1 could be involved in the pathophysiology of iron deficiency anemias or iron overload syndromes, such as hemochromatosis.

As described herein, Ferroportin1 refers to an evolutionarily conserved family of proteins that mediate the transport of iron out of cells. The family includes proteins which are conserved at least as widely as from zebrafish to humans and exhibit very different expression patterns in tissues. Specific embodiments described include Ferroportin1 proteins from mice, humans and zebrafish which have been shown to be functional iron transporters. The term Ferroportin1 can refer to other proteins sharing at least about 70% sequence similarity, more preferably at least about 80% sequence similarity, and still more preferably, at least about 90% sequence similarity, and most preferably, at least about 95% sequence similarity.

One aspect of the invention relates to isolated nucleic acids or polynucleotides that encode a Ferroportin1 as described herein, such as those Ferroportin1 proteins having an amino acid sequence SEQ ID NO:2, SEQ ID NO:4 or SEQ ID NO:6 and nucleic acids closely related thereto as described herein.

Using the information provided herein, such as a nucleic acid sequence set forth in SEQ ID NO:1, SEQ ID NO:3 or SEQ ID NO:5, a nucleic acid of the invention encoding a Ferroportin1 polypeptide may be obtained using standard cloning and screening methods, such as those for cloning and sequencing cDNA library fragments, followed by obtaining a full length clone. For example, to obtain a nucleic acid of the invention, a library of clones of cDNA of a species of animal can be probed with a labeled oligonucleotide, such as a radiolabeled oligonucleotide, preferably about 17 nucleotides or longer, derived from a partial sequence. Clones carrying DNA identical to that of the probe can then be distinguished using stringent (also, "high stringency") hybridization conditions. By sequencing the individual clones thus identified with sequencing primers designed from the original sequence it is then possible to extend the sequence in both directions to determine the full length sequence. Suitable techniques are described, for example, in *Current Protocols in Molecular Biology* (F. M. Ausubel et al., eds.), containing supplements through Supplement 49, 2000, John Wiley and Sons, Inc., especially chapters 5, 6 and 7.

Embodiments of the invention include isolated nucleic acid molecules comprising any of the following nucleotide sequences: 1.) a nucleotide sequence which encodes a protein comprising the amino acid sequence of human Ferroportin1 (SEQ ID NO:6), the amino acid sequence of mouse Ferroportin1 (SEQ ID NO:4), or the amino acid sequence of zebrafish Ferroportin1 (SEQ ID NO:2); 2.) nucleotide sequences of human ferroportin1, mouse ferroportin1, or zebrafish ferroportin1; 3.) a nucleotide sequence which is complementary to the nucleotide sequence of human ferroportin1 (SEQ ID NO:5), mouse ferroportin1 (SEQ ID NO:3), zebrafish ferroportin1 (SEQ ID NO:1); 4.) a nucleotide sequence which consists of the coding region of human ferroportin1 (within SEQ ID NO:5), the coding region of mouse ferroportin1 (within SEQ ID NO:3), or the coding region of zebrafish ferroportin1 (within SEQ ID NO:1).

The invention further relates to nucleic acids (nucleic acid molecules or polynucleotides) having nucleotide sequences identical over their entire length to SEQ ID NO:1, SEQ ID NO:3 or SEQ ID NO: 5. It further relates to DNA, which due to the degeneracy of the genetic code, encodes a Ferroportin1 protein whose amino acid sequence is provided herein. Also provided by the invention are nucleic acids having the coding sequences for the mature polypeptides or fragments in reading frame with other coding sequences, such as those encoding a leader or secretory sequence, a pre-, or pro- or preproprotein sequence. The nucleic acids of the invention encompass nucleic acids that include a single continuous region or discontinuous regions encoding the polypeptide, together with additional regions, that may also contain coding or non-coding sequences. The nucleic acids may also contain non-coding sequences, including, for example, but not limited to, non-coding 5' and 3' sequences, such as the transcribed, non-translated sequences, termination signals, ribosome binding sites, sequences that stabilize mRNA, introns, polyadenylation signals, and additional coding sequences which encode additional amino acids.

The nucleic acid molecules of the invention can comprise, in addition to sequences identified by SEQ ID NO or sequences related to these by variations and by hybridization as described herein, other sequences encoding unrelated (heterologous—that is, with insignificant sequence similarity to a Ferroportin1) polypeptides or peptides. These peptides or polypeptides can be whole proteins, as occur naturally or as have been modified by design. Together, the nucleic acid sequences make up genes for hybrid or fusion proteins. For example, an unrelated marker sequence that facilitates purification (e.g., by affinity column) of the fused polypeptide can be encoded. In certain embodiments of the invention, the marker sequence can be a hexa-histidine peptide, as provided in the pQE vector (Qiagen, Inc.) and described in Gentz et al., Proc. Natl. Acad. Sci. USA 86: 821-824 (1989), or an HA tag (Wilson et al., Cell 37: 767 (1984)), or a sequence encoding glutathione S-transferase of Schistosoma japonicum (vectors available from Pharmacia; see Smith, D. B. and Johnson K. S., Gene 67:31 (1988) and Kaelin, W. G. et al., Cell 70:351 (1992)). For additional applications, the unrelated nucleic acid sequence can encode a peptide or polypeptide which is immunogenic or which enhances the immunogenicity of the fusion protein or polypeptide. Nucleic acids of the invention also include, but are not limited to, nucleic acids comprising a structural gene and its naturally associated sequences that control gene expression.

The invention further relates to variants, including naturally-occurring allelic variants, of those nucleic acids described specifically herein by DNA sequence, that encode variants of such polypeptides as those having the amino acid sequences SEQ ID NO:2, SEQ ID NO:4 or SEQ ID NO:6. Such variants include nucleic acids encoding variants of the above-listed amino acid sequences, wherein those variants have several, such as 5 to 10, 1 to 5, or 3, 2 or 1 amino acids substituted, deleted, or added, in any combination. Variants include polynucleotides encoding polypeptides with at least 95% but less than 100% amino acid sequence identity to the polypeptides described herein by amino acid sequence. Variant polynucleotides hybridize, under low to high stringency conditions, to the alleles described specifically herein by DNA sequence. In one embodiment, variants have silent substitutions, additions and deletions that do not alter the properties and activities of the Ferroportin1. Allelic variants of the polynucleotides encoding human Ferroportin1 (SEQ ID NO:5), mouse Ferroportin1 (SEQ ID NO:3), and zebrafish Ferroportin1 (SEQ ID NO:1) will be identified as mapping to chromosomal locations corresponding to the chromosomal locations of the wild type genes.

Orthologous genes are gene loci in different species that are sufficiently similar to each other in their nucleotide sequences to suggest that they originated from a common ancestral gene. Orthologous genes arise when a lineage splits into two species, rather than when a gene is duplicated within a genome. Proteins that are orthologs are encoded by genes of two different species, wherein the genes are said to be orthologous.

The invention further relates to polynucleotides encoding polypeptides which are orthologous to those polypeptides having a specific amino acid sequence described herein, such as the amino acid sequences (SEQ ID NO:2), (SEQ ID NO:4), and (SEQ ID NO:6). These polynucleotides, which can be called ortholog polynucleotides, encode orthologous polypeptides that can range in amino acid sequence identity to a reference amino acid sequence described herein, from about 65% to less than 100%, but preferably 70% to 80%, more preferably 80% to 90%, and still more preferably 90% to less than 100%. Orthologous polypeptides can also be those polypeptides that range in amino acid sequence similarity to a reference amino acid sequence described herein from about 75% to 100%. The ortholog polynucleotides encode polypeptides that have similar functional characteristics (e.g., iron transport activity) and similar tissue distribution, as appropriate to the organism from which the ortholog polynucleotides can be isolated.

Ortholog polynucleotides can be isolated from (e.g., by cloning or nucleic acid amplification methods) a great number of species, as shown by the sample of Ferroportin1 proteins from evolutionarily divergent species described herein. Ortholog polynucleotides corresponding to SEQ ID NO:1, SEQ ID NO:3, and SEQ ID NO:5 are those which can be isolated from mammals such as rat, dog, chimpanzee, monkey, baboon, pig, rabbit and guinea pig, for example.

Further variants that are fragments of the nucleic acids of the invention may be used to synthesize full-length nucleic acids of the invention, such as by use as primers in a polymerase chain reaction. As used herein, the term primer refers to a single-stranded oligonucleotide which acts as a point of initiation of template-directed DNA synthesis under appropriate conditions (e.g., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term primer site refers to the area of the target DNA to which a primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

Further embodiments of the invention are nucleic acids that are at least 80% identical over their entire length to a nucleic acid described herein, for example a nucleic acid having the nucleotide sequence in SEQ ID NO:1, SEQ ID NO:3, and SEQ ID NO:5. Additional embodiments are nucleic acids, and the complements of such nucleic acids, having at least 90% nucleotide sequence identity to the above-described sequences, and nucleic acids having at least 95% nucleotide sequence identity. In preferred embodiments, DNA of the present invention has 97% nucleotide sequence identity, 98% nucleotide sequence identity, or at least 99% nucleotide sequence identity with the DNA whose sequences are presented herein.

Other embodiments of the invention are nucleic acids that are at least 80% identical in nucleotide sequence to a nucleic acid encoding a polypeptide having an amino acid sequence as set forth in SEQ ID NO:2, SEQ ID NO:4 or SEQ ID NO:6, and nucleic acids that are complementary to such nucleic acids. Specific embodiments are nucleic acids having at least 90% nucleotide sequence identity to a nucleic acid encoding a polypeptide having an amino acid sequence as described in the list above, nucleic acids having at least 95% sequence identity, and nucleic acids having at least 97% sequence identity. Also included in the invention are nucleic acid molecules comprising at least 80%, 90%, 95%, or 97% of the coding region of any of SEQ ID NOs 1, 3 or 5.

The terms "complementary" or "complementarity" as used herein, refer to the natural binding of polynucleotides under permissive salt and temperature conditions by base-pairing. Complementarity between two single-stranded molecules may be "partial" in which only some of the nucleic acids bind, or it may be complete when total complementarity exists between the single-stranded molecules (that is, when A-T and G-C base pairing is 100% complete). The degree of complementarity between nucleic acid strands has significant effects on the efficiency and strength of hybridization between nucleic acid strands. This is of particular importance in amplification reactions, which depend on binding between nucleic acid strands.

The invention further includes nucleic acids that hybridize to the above-described nucleic acids, especially those nucleic acids that hybridize under stringent hybridization conditions. Preferred nucleic acid molecules meeting these hybridization criteria also encode a polypeptide having an iron transport function. "Stringent hybridization conditions" or "high stringency conditions" generally occur within a range from about $T_m$ minus 5° C. (5° C. below the strand dissociation temperature or melting temperature ($T_m$) of the probe nucleic acid molecule) to about 20° C. to 25° C. below $T_m$. As will be understood by those of skill in the art, the stringency of hybridization may be altered in order to identify or detect molecules having identical or related polynucleotide sequences. An example of high stringency hybridization follows. Hybridization solution is (6×SSC/10 mM EDTA/0.5% SDS/5×Denhardt's solution/100 µg/ml sheared and denatured salmon sperm DNA). Hybridization is at 64-65° C. for 16 hours. The hybridized blot is washed two times with 2×SSC/0.5% SDS solution at room temperature for 15 minutes each, and two times with 0.2×SSC/0.5% SDS at 65° C., for one hour each. Further examples of high stringency conditions can be found on pages 2.10.1-2.10.16 (see particularly 2.10.8-11) and pages 6.3.1-6 in *Current Protocols in Molecular Biology* (Ausubel, F. M. et al., eds., containing supplements up through Supplement 49, 2000). Examples of high, medium, and low stringency conditions can be found on pages 36 and 37 of WO 98/40404, which are incorporated herein by reference.

The invention further relates to nucleic acids obtainable by screening an appropriate library with a probe having a nucleotide sequence such as that set forth in SEQ ID NO:1, SEQ ID NO:3, and SEQ ID NO:5, or a probe which consists of the coding region of any of these SEQ ID NOs, or a probe which is a sufficiently long fragment of any of the above; and isolating the nucleic acid. Such probes generally can comprise at least 15 nucleotides. Nucleic acids obtainable by such screenings may include RNAs, cDNAs and genomic DNA, for example, encoding iron transport proteins of the Ferroportin1 protein family described herein.

Other nucleic acid embodiments are those comprising a nucleotide sequence encoding a contiguous portion of a polypeptide represented as having amino acid sequence SEQ ID NO:2, SEQ ID NO:4 or SEQ ID NO:6, wherein the portion is at least about 15 amino acids long, but can alternatively be at least 30 amino acids long or 60 amino acids long. The portion can be derived from amino acid sequence at the N-terminal, C-terminal or internal regions of SEQ ID NOs 2, 4 or 6.

Further uses for the nucleic acid molecules of the invention, whether encoding a full-length Ferroportin1 protein or whether comprising a contiguous portion of a nucleic acid molecule such as one given in SEQ ID NO:1, 3 or 5, include use as markers for tissues in which the encoded protein is preferentially expressed (to identify constitutively expressed proteins or proteins produced at a particular stage of tissue differentiation or stage of development of a disease state); as molecular weight markers on southern gels; as chromosome markers or tags (when labeled, for example with biotin, a radioactive label or a fluorescent label) to identify chromosomes or to map related gene positions; to compare with endogenous DNA sequences in a mammal to identify potential genetic disorders; as probes to hybridize and thus identify, related DNA sequences; as a source of information to derive PCR primers for genetic fingerprinting; as a probe to "subtract-out" known sequences in the process of discovering other novel nucleic acid molecules; for selecting and making oligomers for attachment to a "gene chip" or other support, to be used, for example, for examination of expression patterns in embryonic development or in organs of an animal at a particular developmental stage.

Further methods to obtain nucleic acids encoding Ferroportin1 proteins include PCR and variations thereof (e.g., "RACE" PCR and semi-specific PCR methods). Portions of the nucleic acids having a nucleotide sequence set forth in SEQ ID NO:1, SEQ ID NO:3 or SEQ ID NO:5, (especially "flanking sequences" on either side of a coding region) can be used as primers in methods using the polymerase chain reaction, to produce DNA from an appropriate template nucleic acid.

Once a fragment of the ferroportin1 gene is generated by PCR, it can be sequenced, and the sequence of the product can be compared to other DNA sequences, for example, by using the BLAST Network Service at the National Center for Biotechnology Information. The boundaries of the open reading frame can then be identified using semi-specific PCR or other suitable methods such as library screening. Once the 5' initiator methionine codon and the 3' stop codon have been identified, a PCR product encoding the full-length gene can be generated using cDNA as a template (the cDNA being generated from mRNA), with primers complementary to the extreme 5' and 3' ends of the gene or to their flanking sequences. The full-length genes can then be cloned into expression vectors for the production of functional proteins.

In some embodiments of the invention, the nucleic acid molecules can be modified at the base moiety, sugar moiety or phosphate backbone to change the stability, hybridization or solubility properties of the molecules. For example, the deoxyribose phosphate backbone of the nucleic acids can be modified to generate peptide nucleic acids, or PNAs (Hyrup et al., *Bioorganic and Medicinal Chemistry* 4:5-23, 1996). PNAs are nucleic acid mimics in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described by Hyrup et al. (1996) and Perry-O'Keefe et al., *Proc. Natl. Acad. Sci. USA* 93:14670-14675, 1996. PNAs can be used in place of nucleic acids for some applications, for example, as probes or primers for DNA sequence analysis and hybridization, or as antisense agents for sequence-specific modulation of gene expression.

Nucleic acid molecules of the present invention can be incorporated into various constructs (e.g., plasmids, bacteriophages, viruses, artificial chromosomes) and incorporated into host cells in these constructs or in one or more chromosomes of the host cell, for example, for further manipulation of the sequences or for production of an encoded polypeptide under suitable conditions for the growth or maintenance of the cells.

A host cell is a cell, or a descendant thereof, which has been transfected by an exogenous DNA sequence using methods within the skill of those in the art. See, e.g., Graham et al. (1973) *Virology* 52:456, Sambrook et al. (1989) *Molecular Cloning: a Laboratory Manual*, Cold Spring Harbor Laboratories, New York, Davis et al. (1986) *Basic Methods in Molecular Biology*, Elsevier, and Chu et al. (1981) *Gene* 13:197. More particularly, there are two major steps in transfection: first, the exogenous DNA must traverse the recipient (host) cell plasma membrane in order to be exposed to the cell's transcription and replication machinery; and second, the DNA must either become stably integrated into the host cell genome, or be capable of extra-chromosomal replication at a sufficient rate. A number of transfection methods have been described in the art, such as calcium phosphate co-precipitation (Graham et al. (1973) *Virol.* 52:456-467), direct micro-injection into cultured cells (Capecchi, M. R. (1980) *Cell* 22:479-488), electroporation (Shigekawa et al. (1988) *BioTechniques* 6:742-751), liposome mediated gene transfer (Mannino et al. (1988) *BioTechniques* 6:682-690), lipid-mediated transfection (Felgner et al. (1987) *Proc. Natl. Acad. Sci. USA* 84:7413-7417), and nucleic acid delivery using high-velocity microprojectiles (Klein et al. (1987) *Nature* 327:70-73).

The invention also relates to isolated proteins or polypeptides such as those encoded by nucleic acids of the present invention. Isolated proteins can be purified from a natural source or can be made recombinantly. Proteins or polypeptides referred to herein as "isolated" are proteins or polypeptides that exist in a state different from the state in which they exist in cells in which they are normally expressed in an organism, and include proteins or polypeptides obtained by methods described herein, similar methods or other suitable methods, and also include essentially pure proteins or polypeptides, proteins or polypeptides produced by chemical synthesis or by combinations of biological and chemical methods, and recombinant proteins or polypeptides which are isolated. Thus, the term "isolated" as used herein, indicates that the polypeptide in question exists in a physical milieu distinct from that in which it occurs in nature. Thus, "isolated" includes existing in membrane fragments and vesicles, membrane fractions, liposomes, lipid bilayers and other artificial membrane systems. An isolated Ferroportin1 may be substantially isolated with respect to the complex cellular milieu in which it naturally occurs, and may even be purified essentially to homogeneity, for example as determined by PAGE or column chromatography (for example, HPLC), but may also have further cofactors or molecular stabilizers, such as detergents, added to the purified protein to enhance activity. In one embodiment, proteins or polypeptides are isolated to a state at least about 75% pure; more preferably at least about 85% pure, and still more preferably at least about 95% pure, as determined by Coomassie blue staining of proteins on SDS-polyacrylamide gels. Proteins or polypeptides referred to herein as "recombinant" are proteins or polypeptides produced by the expression of recombinant nucleic acids.

"Polypeptide" as used herein indicates a molecular chain of amino acids and does not refer to a specific length of the product. Thus, peptides, oligopeptides and proteins are included within the definition of polypeptide. This term is also intended to include polypeptide that have been subjected to post-expression modifications such as, for example, glycosylations, acetylations, phosphorylations and the like.

In a preferred embodiment, an isolated polypeptide comprising a Ferroportin1, a functional portion thereof, or a functional equivalent of the Ferroportin1, has at least one function characteristic of a Ferroportin1, for example, transport activity, binding function (e.g., a domain which binds to a cofactor), or antigenic function (e.g., binding of antibodies that also bind to a naturally-occurring Ferroportin1, as that function is found in an antigenic determinant). Functional equivalents can have activities that are quantitatively similar to, greater than, or less than, the reference protein. These proteins include, for example, naturally occurring Ferroportin1 proteins that can be purified from tissues in which they are produced (including polymorphic or allelic variants), variants (e.g., mutants) of those proteins and/or portions thereof. Such variants include mutants differing by the addition, deletion or substitution of one or more amino acid residues, or modified polypeptides in which one or more residues are modified, and mutants comprising one or more modified residues. The portions of the invention also include isolated polypeptides encoded by a nucleic acid molecule, wherein said nucleic acid molecule hybridizes to a complement of any of SEQ ID NO:1, SEQ ID NO:3 or SEQ ID NO:5 under high stringency conditions. Portions or fragments of a Ferroportin1 can range in size from ten amino acid residues to the entire amino acid sequence minus one amino acid. An isolated polypeptide comprising a functional portion of a Ferroportin1 can comprise at least 10 amino acid residues of a cytoplasmic or extracellular domain of a Ferroportin1.

The isolated proteins of the invention preferably include mammalian iron transport proteins of the Ferroportin1 family of homologous proteins. In preferred embodiments, the extent of amino acid sequence identity between a polypeptide having one of the amino acid sequences SEQ ID NO:2, SEQ ID NO:4 or SEQ ID NO:6, and the respective functional equivalents of these polypeptides is at least about 80% or 88%. In other embodiments, the degree of amino acid sequence identity between a Ferroportin1 and its respective functional equivalent is at least about 91%, at least about 94%, or at least about 97%.

The polypeptides of the invention also include those Ferroportin1 proteins encoded by polynucleotides which are orthologous to those polynucleotides, the sequences of which are described herein in whole or in part. Ferroportin1 proteins which are orthologs to those described herein by amino acid sequence, in whole or in part, are, for example, Ferroportin1 proteins of dog, rat, chimpanzee, monkey, rabbit, guinea pig, baboon and pig, and are also embodiments of the invention.

To determine the percent identity of two amino acid sequences or of two nucleic acid sequences, the sequences are aligned for optimal comparison. In the simplest concept of identity, two nucleic acid sequences or two amino acid sequences are compared after aligning them for the maximum number of matches at the same position, without the introduction of any gaps. In a somewhat more complex concept of identity, the sequences are aligned and gaps can be introduced in one or both of a first and a second amino acid or nucleic acid sequence for optimal alignment, and non-homologous (dissimilar) sequences can be disregarded for comparison purposes. In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity in terms of structure and chemical characteristics so as to perform one or more of the same functions performed by the polypeptides described herein by amino acid sequence. Similarity for a polypeptide is determined by amino acid substitutions, which can be conservative amino acid substitutions. For example, the invention encompasses polypeptides with at least one conservative amino acid substitution. Conservative substitutions are those that replace a given amino acid residue in a polypeptide with another amino acid residue of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr and Trp. Guidance concerning which amino acid changes are likely to be phenotypically silent is found in Bowie et al., *Science* 247:1306-1310 (1990).

TABLE

| Conservative Amino Acid Substitutions | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent similarity between two sequences can be accomplished using a mathematical algorithm. (*Computational Molecular Biology*, Lesk, A. M., ed., Oxford University Press, New York, 1988; *Biocomputing. Informatics and Genome Projects*, Smith, D. W., ed., Academic Press, New York, 1993; *Computer Analysis of sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereaux, J., eds., M. Stockton Press, New York, 1991). In a preferred embodiment, the percent similarity between two amino acid sequences is determined using the Needleman and Wunsch (*J. Mol. Biol.* (48):444-453 (1970)) algorithm which has been incorporated into the GAP program in the Wisconsin Package Version 10.0, Genetics Computer Group (GCG), Madison Wis., using, for example, a PAM250 matrix, and a gap weight of 16, 14, 12, 10, 8, 6, or 4 and a length weight of 1, 2, 3, 4, 5, or 6. In yet another preferred embodiment, the percent similarity between two nucleotide sequences is determined using the GAP program in the Wisconsin Package (Devereux, J., et al., *Nucleic Acids Res.* 12(1): 387 (1984)), using a NWSgapdna.CMP matrix and a gap weight of 40, 50, 60, 70, or 80 and a length weight of 1, 2, 3, 4, 5, or 6. In another embodiment, the percent similarity between two amino acid or nucleotide sequences is determined using the algorithm of E. Meyers and W. Miller (*CABIOS*, 4:11-17 (1989)) which has been incorporated into the ALIGN program (version 2.0), using a PAM120 weight residue table, a gap length penalty of 12 and a gap penalty of 4.

The nucleic acids and protein sequences of the present invention can further be used as a "query sequence" to perform a search against databases to, for example, identify other family members or related sequences. Such searches can be performed using the BLASTN, BLASTP, BLASTX, TBLASTN, TBLASTX programs (version 2.0) or PSI-BLAST 2.1 programs based on Altschul, et al. (*J. Mol. Biol.* 215:403-10 (1990)). BLAST nucleotide searches can be performed with the BLASTN program, for example, with default parameters matrix=BIOSUM62, gap existence cost=11, per residue gap cost=1, lambda ratio=0.85, filtered, to obtain nucleotide sequences homologous to (with calculatably significant similarity to) the nucleic acid molecules of the invention. BLAST protein searches can be performed with the BLASTP program, for example, with default parameters scoring matrix=BIOSUM62, word size=3, E value=10, gap costs=11.1 and alignments=50, to obtain amino acid sequences homologous to the proteins of the invention. To obtain gapped alignments for comparison purposes, Gapped BLAST can be utilized as described in Altschul et al., (*Nucleic Acids Res.* 25(17):3389-3402 (1997)). When utilizing BLAST and gapped BLAST programs, the default parameters of the respective programs (e.g., XBLAST and NBLAST) can be used.

Within the invention are isolated nucleic acid molecules having at least 80%, 85%, 90%, 95% and 97% sequence similarity to a nucleic acid encoding a polypeptide comprising the amino acid sequence SEQ ID NO:2, SEQ ID NO:4 or SEQ ID NO:6. Also within the invention are isolated nucleic acid molecules which hybridize under high stringency conditions to nucleic acid consisting of the coding regions of SEQ ID NO:1, SEQ ID NO:3 or SEQ ID NO:5.

The invention further relates to fusion proteins, comprising a Ferroportin1 or functional portion thereof (as described above) as a first moiety, linked to second moiety or to multiple moieties not occurring in the Ferroportin1 as found in nature. Thus, a second moiety can be an amino acid, peptide or polypeptide. The second moiety can be in an N-terminal location, C-terminal location or internal to the fusion protein, or multiple heterologous moieties can be in multiple locations. In one embodiment, the fusion protein comprises a Ferroportin1 or portion thereof having iron transport function as the first moiety, and a second moiety comprising a linker sequence and an affinity ligand. Fusion proteins can be produced by a variety of methods. For example, a fusion protein can be produced by the insertion of a ferroportin1 gene or portion thereof into a suitable expression vector, such as Bluescript SK+/− (Stratagene), pGEX-4T-2 (Pharmacia), pET-24(+) (Novagen), or vectors of similar construction. The resulting construct can be introduced into a suitable host cell for expression. Upon expression, fusion protein can be purified from cells by means of a suitable affinity matrix (See e.g., *Current Protocols in Molecular Biology*, Ausubel, F. M. et al., eds., Vol. 2, pp. 16.4.1-16.7.8, containing supplements up through Supplement 49, 2000).

The invention also relates to enzymatically produced, synthetically produced, or recombinantly produced portions of a Ferroportin1 protein. Portions of a Ferroportin1 can be made which have full or partial function on their own, or which when mixed together (though fully, partially, or nonfunctional alone), spontaneously assemble with one or more other polypeptides to reconstitute a functional protein having at least one function characteristic of a Ferroportin1.

Fragments of a Ferroportin1 can be produced by direct peptide synthesis, for example those using solid-phase techniques (Roberge, J. Y. et al., *Science* 269:202-204 (1995); Merrifield, J., *J. Am. Chem. Soc.* 85:2149-2154 (1963)). Peptide or polypeptide synthesis can be performed using manual techniques or by automation. Automated synthesis can be carried out using, for instance, an Applied Biosystems 431A Peptide Synthesizer (Perkin Elmer). Various fragments of a Ferroportin1 can be synthesized separately and combined using chemical methods.

One aspect of the invention is a peptide or polypeptide having the amino acid sequence of a portion of a Ferroportin1 protein which is hydrophilic rather than hydrophobic, and ordinarily can be detected as facing the outside of the cell membrane. Such a peptide or polypeptide can be thought of as being an extracellular domain of the Ferroportin1, or a mimetic of said extracellular domain. Peptides or polypeptides comprising at least 10 amino acid residues of a cytoplasmic or extracellular domain of human, mouse or zebrafish Ferroportin1 can be synthesized.

The term "mimetic" as used herein, refers to a molecule, the structure of which is developed from knowledge of the structure of the Ferroportin1 of interest, or one or more portions thereof, and, as such, is able to effect some or all of the functions of a Ferroportin1.

Portions of a Ferroportin1 can be prepared by enzymatic cleavage of the isolated protein, or can be made by chemical synthesis methods. Portions of a Ferroportin1 can also be made by recombinant DNA methods in which restriction fragments, or fragments that may have undergone further enzymatic processing, or synthetically made DNAs are joined together to construct an altered ferroportin1 gene. The gene can be made such that it encodes one or more desired portions of a Ferroportin1. These portions of Ferroportin1 can be entirely homologous to a known Ferroportin1, or can be altered in amino acid sequence relative to naturally occurring Ferroportin1 proteins to enhance or introduce desired properties such as solubility, stability, or affinity to a ligand. A further feature of the gene can be a sequence encoding an N-terminal signal peptide directed to the plasma membrane.

Another aspect of the invention relates to a method of producing a Ferroportin1 protein, variants or portions thereof, and to expression systems and host cells containing a vector appropriate for expression of a Ferroportin1 protein.

Cells that express a Ferroportin1, a variant or a portion thereof, or an ortholog of a Ferroportin1 described herein by amino acid sequence, can be made and maintained in culture, under conditions suitable for expression, to produce protein in the cells for cell-based assays, or to produce protein for isolation. These cells can be procaryotic or eucaryotic. Examples of procaryotic cells that can be used for expression include *Escherichia coli, Salmonella typhimurium* and *Bacillus subtilis*. Examples of eucaryotic cells that can be used for expression include yeasts such as *Saccharomyces cerevisiae, Schizosaccharomyces pombe, Pichia pastoris* and other lower eucaryotic cells, and cells of higher eucaryotes such as those from insects and mammals, such as primary cells and cell lines such as CHO, HeLa, 3T3, BHK, COS, human kidney 293 and Jurkat cells. (See, e.g., Ausubel, F. M. et al., eds. *Current Protocols in Molecular Biology*, Greene Publishing Associates and John Wiley & Sons, Inc., containing Supplements up through Supplement 49, 2000)).

In one embodiment, host cells that produce a recombinant Ferroportin1, or a portion thereof, a variant, or an ortholog of a Ferroportin1 described herein by amino acid sequence, can be made as follows. A gene encoding a Ferroportin1, variant or a portion thereof can be inserted into a nucleic acid vector, e.g., a DNA vector, such as a plasmid, phage, cosmid, phagemid, virus, virus-derived vector (e.g., SV40, vaccinia, adenovirus, fowl pox virus, pseudorabies viruses, retroviruses) or other suitable replicon, which can be present in a single copy or multiple copies, or the gene can be integrated in a host cell chromosome. A suitable replicon or integrated gene can contain all or part of the coding sequence for a Ferroportin1 or variant, operably linked to one or more expression control regions whereby the coding sequence is under the control of transcription signals and linked to appropriate translation signals to permit translation. The vector can be introduced into cells by a method appropriate to the type of host cells (e.g., transfection, electroporation, infection). For expression from the Ferroportin1 gene, the host cells can be maintained under appropriate conditions (e.g., in the presence of inducer, normal growth conditions, etc.). Proteins or polypeptides thus produced can be recovered (e.g., from the cells, as in a membrane fraction, from the periplasmic space of bacteria, from culture medium) using suitable techniques. Appropriate membrane targeting signal peptides may be incorporated into the expressed polypeptide. These signals may be endogenous to the polypeptide or they may be heterologous signal peptides that do no naturally occur with a Ferroportin1.

Polypeptides of the invention can be recovered and purified from cell cultures (or from their primary cell source) by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and high performance liquid chromatography. Known methods for refolding protein can be used to regenerate active conformation if the polypeptide is denatured during isolation or purification.

The host cells of the invention can be used to produce nonhuman transgenic animals. For example, in one embodiment, a host cell of the invention is a fertilized oocyte or an embryonic stem cell into which Ferroportin1 coding sequences have been introduced. Such host cells can then be used to create non-human transgenic animals in which exogenous ferroportin1 sequences have been introduced into their genome, or homologous recombinant animals in which endogenous ferroportin1 sequences have been altered. Such animals are useful for studying the function and/or activity of Ferroportin1, and for identifying and/or evaluating modulators of Ferroportin1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. "Exogenous" as used in the context of a transgenic animal, means different from that of the unaltered recipient host cell. As used herein, a "homologous recombinant animal" is a non-human animal, preferably a mammal, more preferably a mouse, in which an endogenous weh gene has been altered by homologous recombination between the endogenous gene and an exogenous DNA molecule introduced into a cell of the animal, e.g., an embryonic cell of the animal, prior to development of the animal.

A transgenic animal of the invention can be created by introducing Ferroportin1 encoding nucleic acid into the male pronuclei of a fertilized oocyte, e.g., by microinjection, retroviral infection, and allowing the oocyte to develop in a pseudopregnant female foster animal. The ferroportin1 cDNA sequence can be introduced as a transgene into the genome of a non-human animal. Alternatively, a nonhuman homolog of the human ferroportin1 gene can be isolated based on hybridization to the human or mouse ferroportin1 cDNA and used as a transgene. Intronic sequences and polyadenylation signals can also be included in the transgene to increase the efficiency of expression of the transgene. One or more tissue-specific regulatory sequences can be operably linked to the ferroportin1 transgene to direct expression of Ferroportin1 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the ferroportin1 transgene in its genome and/or expression of ferroportin1 mRNA in tissues or cells of the animals. A transgenic founder animal can then be used to breed additional animals carrying the transgene. Transgenic animals carrying a transgene encoding Ferroportin1 can further be bred to other transgenic animals carrying other transgenes.

To create a homologous recombinant animal, a vector is prepared which contains at least a portion of a ferroportin1 gene (e.g., a human or a non-human homolog of the gene encoding Ferroportin1, e.g., a murine ferroportin1 gene) into which a deletion, addition or substitution has been introduced to thereby alter, e.g., functionally disrupt, the ferroportin1 gene. In a preferred embodiment, the vector is designed such that, upon homologous recombination, the endogenous ferroportin1 gene is functionally disrupted (i.e., no longer encodes a functional protein; also referred to as a "knock out" vector).

Alternatively, the vector can be designed such that, upon homologous recombination, the endogenous ferroportin1 gene is mutated or otherwise altered but still encodes functional protein (e.g., the upstream regulatory region can be altered to thereby alter the expression of the endogenous Ferroportin1 protein). In the homologous recombination vector, the altered portion of the ferroportin1 gene is flanked at its 5' and 3' ends by additional nucleic acid of the ferroportin1 gene to allow for homologous recombination to occur between the exogenous ferroportin1 gene carried by the vector and an endogenous ferroportin1 gene in an embryonic stem cell. The additional flanking ferroportin1 nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced ferroportin1 gene has homologously recombined with the endogenous ferroportin1 gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage PI. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

In a further aspect of the invention are methods for assessing the transport function of any of the Ferroportin1 proteins or polypeptides described herein, including orthologs, and in variations of these, methods for identifying an inhibitor (or an enhancer) of such function and methods for assessing the transport function in the presence of a candidate inhibitor or a known inhibitor.

A variety of systems comprising living cells can be used for these methods. Cells to be used in iron transport assays, and further in methods for identifying an inhibitor or enhancer of this function, express one or more Ferroportin1 proteins. Cells for use in cell-based assays described herein can be drawn from a variety of sources, such as isolated primary cells of various organs and tissues wherein a Ferroportin1 protein is naturally expressed. In some cases, the cells can be from adult organs, and in some cases, from embryonic or fetal structures, such as placenta, yolk sac, heart, lung, liver, intestine, skeletal muscle, kidney and the like. Cells for this purpose can also include cells cultured as fragments of organs or in conditions simulating the cell type and/or tissue organization of organs, in which artificial materials may be used as substrates for cell growth. Other types of cells suitable for this purpose include cells of a cell strain or cell line (ordinarily comprising cells considered to be "transformed") transfected to express one or more types of Ferroportin1.

A further embodiment of the invention is a method for detecting, in a sample of cells, a Ferroportin1 protein, a portion or fragment thereof, a fusion protein comprising a Ferroportin1 or a portion thereof, or an ortholog as described herein, wherein the cells can be, for instance, cells of a tissue, primary culture cells, or cells of a cell line, including cells into which nucleic acid has been introduced. The method comprises adding to the sample an agent that specifically binds to the protein, and detecting the agent specifically bound to the protein. Appropriate washing steps can be added to reduce nonspecific binding to the agent. The agent can be, for example, an antibody, a ligand or a substrate or cofactor mimic. The agent can have incorporated into it, or have bound to it, covalently or by high affinity non-covalent interactions, for instance, a label that facilitates detection of the agent to which it is bound, wherein the label can be, but is not limited to, a phosphorescent label, a fluorescent label, a biotin or avidin label, or a radioactive label. The means of detection of a Ferroportin1 can vary, as appropriate to the agent and label used. For example, for an antibody that binds to the Ferroportin1, the means of detection may call for binding a second antibody, which has been conjugated to an enzyme, to the antibody which binds the Ferroportin1, and detecting the presence of the second antibody by means of the enzymatic activity of the conjugated enzyme.

Similar principles can also be applied to a cell lysate, membrane fraction, or a more purified preparation of proteins from cells that may comprise a Ferroportin1 protein of interest, for example in the methods of immunoprecipitation, immunoblotting, immunoaffinity methods, that in addition to detection of the particular Ferroportin1, can also be used in purification steps, and qualitative and quantitative immunoassays. See, for instance, chapters 11 through 14 in *Antibodies: A Laboratory Manual*, E. Harlow and D. Lane, eds., Cold Spring Harbor Laboratory, 1988.

Isolated Ferroportin1 protein or, an antigenically similar portion thereof, especially a portion that is soluble (e.g., a peptide or a fusion polypeptide comprising at least 10 contiguous amino acid residues of a Ferroportin1), can be used in a method to select and identify molecules which bind specifically to the Ferroportin1. Fusion proteins comprising all of, or a portion of, the Ferroportin1 linked to a second moiety not occurring in the Ferroportin1 as found in nature, can be prepared for use in another embodiment of the method. Suitable fusion proteins for this purpose include those in which the second moiety comprises an affinity ligand (e.g., an enzyme, antigen, epitope). Ferroportin1 fusion proteins can be produced by the insertion of a gene encoding the Ferroportin1 or a variant thereof, or a suitable portion of such gene into a suitable expression vector which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix.

In one embodiment, the fusion protein can be immobilized on a suitable affinity matrix under conditions sufficient to bind the affinity ligand portion of the fusion protein to the matrix, and is contacted with one or more candidate binding agents (e.g., a mixture of peptides or compounds of a library) to be tested, under conditions suitable for binding of the binding agents to the Ferroportin1 portion of the bound fusion protein. Next, the affinity matrix with bound fusion protein can be washed with a suitable wash buffer to remove unbound candidate binding agents and non-specifically bound candidate binding agents. Those agents which remain bound can be released by contacting the affinity matrix with fusion protein bound thereto with a suitable elution buffer. Wash buffer can be formulated to permit binding of the fusion protein to the affinity matrix, without significantly disrupting binding of specifically bound binding agents. In this aspect, elution buffer can be formulated to permit retention of the fusion protein by the affinity matrix, but can be formulated to interfere with binding of the candidate binding agents to the target portion of the fusion protein. For example, a change in the ionic strength or pH of the elution buffer can lead to release of specifically bound agent, or the elution buffer can comprise a release component or components designed to disrupt binding of specifically bound agent to the target portion of the fusion protein.

Immobilization can be performed prior to, simultaneous with, or after, contacting the fusion protein with candidate binding agent, as appropriate. Various permutations of the method are possible, depending upon factors such as the candidate molecules tested, the affinity matrix-ligand pair selected, and elution buffer formulation. For example, after the wash step, fusion protein with binding agent molecules bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with the candidate agent bound thereto. Bound agent molecules can then be released from the fusion protein or its cleavage product by an appropriate method, such as extraction.

One or more candidate binding agents can be tested simultaneously. Where a mixture of candidate binding agents is tested, those found to bind by the foregoing processes can be separated (as appropriate) and identified by suitable methods (e.g., PCR, sequencing, chromatography). Large libraries of candidate binding agents produced by combinatorial chemical synthesis or by other methods can be tested (see e.g., Ohlmeyer, M. H. J. et al., *Proc. Natl. Acad. Sci. USA* 90:10922-10926 (1993) and DeWitt, S. H. et al., *Proc. Natl. Acad. Sci. USA* 90:6909-6913 (1993), relating to tagged compounds; see also Rutter, W. J. et al. U.S. Pat. No. 5,010,175; Huebner, V. D. et al., U.S. Pat. No. 5,182,366; and Geysen, H. M., U.S. Pat. No. 4,833,092). Where binding agents selected from a combinatorial library by the present method carry unique tags, identification of individual biomolecules by chromatographic methods is possible. Where binding agents do not carry tags, chromatographic separation, followed by mass spectrometry to ascertain structure, can be used to identify binding agents selected by the method, for example.

The invention also comprises a method for identifying an agent which inhibits interaction between a Ferroportin1 protein (e.g., one comprising the amino acid sequence in SEQ ID NO:2, SEQ ID NO:4 or SEQ ID NO:6), and a ligand of said protein. The Ferroportin1 can be one described by amino acid sequence herein, a portion or fragment thereof, a variant thereof, or an ortholog thereof, or a Ferroportin1 fusion protein. Here, a ligand can be, for instance, a substrate (e.g., $Fe^{2+}$), or a substrate mimic, an antibody, or a compound, such as a small molecule or peptide, that binds with specificity to a site on the protein. The method comprises combining, not limited to a particular order, the Ferroportin1 protein, the ligand of the protein, and a candidate agent to be assessed for its ability to inhibit interaction between the protein and the ligand, under conditions appropriate for interaction between the protein and the ligand (e.g., pH, salt, temperature conditions conducive to appropriate conformation and molecular interactions); determining the extent to which the protein and ligand interact; and comparing (1) the extent of protein-ligand interaction in the presence of candidate agent with (2) the extent of protein-ligand interaction in the absence of candidate agent, wherein if (1) is less than (2), then the candidate agent is one which inhibits interaction between the protein and the ligand.

The method can be facilitated, for example, by using an experimental system which employs a solid support (column chromatography matrix, wall of a plate, microtiter wells, column pore glass, pins to be submerged in a solution, beads, etc.) to which the protein can be attached. Accordingly, in one embodiment, the protein can be fixed to a solid phase directly or indirectly, by a linker. The candidate agent to be tested is added under conditions conducive for interaction and binding to the protein. The ligand is added to the solid phase system under conditions appropriate for binding. Excess ligand is removed, as by a series of washes done under conditions that do not disrupt protein-ligand interactions. Detection of bound ligand can be facilitated by using a ligand that carries a label (e.g., fluorescent, chemiluminescent, radioactive). In a control experiment, protein and ligand are allowed to interact in the absence of any candidate agent, under conditions otherwise identical to those used for the "test" conditions where candidate inhibiting agent is present, and any washes used in the test conditions are also used in the control. The extent to which ligand binds to the protein in the presence of candidate agent is compared to the extent to which ligand binds to the protein in the absence of the candidate agent. If the extent to which interaction of the protein and the ligand occurs is less in the presence of the candidate agent than in the absence of the candidate agent, the candidate agent is an agent which inhibits interaction between the protein and the ligand of the protein.

In a further embodiment, an inhibitor (or an enhancer) of a Ferroportin1 protein can be identified. The method comprises steps which are, or are variations of, the following: contacting the cells with $Fe^{2+}$ under conditions allowing uptake of the $Fe^{2+}$, wherein the $Fe^{2+}$ can be labeled for convenience of detection; washing away extracellular $Fe^{2+}$, contacting a first aliquot of the cells with an agent being tested as an inhibitor (or enhancer) of iron export, while maintaining a second aliquot of cells under the same conditions but without contact with the agent; and determining (e.g., by a quantitative measurement) iron exported from the first and second aliquots of cells; wherein a lesser quantity of iron in the first aliquot compared to that in the second aliquot is indicative that the agent is an inhibitor of iron export by a Ferroportin1 protein. A greater quantity of extracellular iron found in the first aliquot compared to that in the second aliquot is indicative that the agent is an enhancer of iron export by a Ferroportin1 protein.

A particular embodiment of identifying an inhibitor or enhancer of iron export function employs the above steps, but also employs additional steps preceding those given above: introducing into cells of a cell strain or cell line ("host cells" for the intended introduction of, or after the introduction of, a vector) one or more vectors or RNAs comprising a ferroportin1 gene, wherein expression of the gene can be regulatable or constitutive, and providing conditions to the host cells under which expression of the gene can occur, and under which iron can be taken up by the host cells.

The terms "contacting" and "combining" as used herein in the context of bringing molecules into close proximity to each other, can be accomplished by conventional means. For example, when referring to molecules that are soluble, contacting is achieved by adding the molecules together in a solution. "Contacting" can also be adding an agent to a test system, such as a vessel containing cells in tissue culture.

The term "inhibitor" or "antagonist", as used herein, refers to an agent which blocks, diminishes, inhibits, hinders, limits, decreases, reduces, restricts or interferes with iron export from a cell, or alternatively or additionally, prevents or impedes the cellular effects associated with iron export. The term "enhancer" or "agonist", as used herein, refers to an agent which augments, enhances, or increases iron export from a cell.

In order to produce a "host cell" type suitable for iron uptake assays and for assays derived therefrom for identifying inhibitors or enhancers thereof, a nucleic acid vector can be constructed to comprise a gene encoding an iron transport protein, for example, human Ferroportin1, a mutant or variant thereof, an ortholog of the human protein, such as porcine or bovine orthologs or orthologs found in other mammals, or a Ferroportin1 family protein of origin in an organism other than a mammal. The gene of the vector can be regulatable, such as by the placement of the gene under the control of an inducible or repressible promoter in the vector (e.g., inducible or repressible by a change in growth conditions of the host cell harboring the vector, such as addition of inducer, binding or functional removal of repressor from the cell millieu, or change in temperature) such that expression of the ferroportin1 gene can be turned on or initiated by causing a change in growth conditions, thereby causing the protein encoded by the gene to be produced, in host cells comprising the vector, as a plasma membrane protein. Alternatively, the ferroportin1 gene can be constitutively expressed.

A vector comprising a ferroportin1 gene, such as a vector described herein, can be introduced into host cells by a means appropriate to the vector and to the host cell type. For example, commonly used methods such as electroporation, transfection, for instance, transfection using $CaCl_2$, and transduction (as for a virus or bacteriophage) can be used. Host cells can be, for example, mammalian cells such as primary culture cells or cells of cell lines such as COS cells, 293 cells or Jurkat cells. Host cells can also be, in some cases, cells derived from insects, cells of insect cell lines, bacterial cells, such as *E. coli*, or yeast cells, such as *S. cerevisiae*. It is preferred that the iron export protein whose function is to be assessed, with or without a candidate inhibitor or enhancer, be produced in host cells whose ancestor cells originated in a species related to the species of origin of the ferroportin1 gene encoding the Ferroportin1 protein. For example, it is preferable that tests of function or of inhibition or enhancement of a mammalian Ferroportin1 be carried out in host mammalian cells producing the Ferroportin1, rather than in bacterial cells or yeast cells.

Host cells comprising a vector comprising a regulatable ferroportin1 gene can be treated so as to allow expression of the ferroportin1 gene and production of the encoded protein (e.g., by contacting the cells with an inducer compound that effects transcription from an inducible promoter operably linked to the ferroportin1 gene).

The test agent (e.g., an agonist or antagonist) is added to the cells to be used in an iron export assay, under conditions suitable for production and/or maintenance of the expressed Ferroportin1 in a conformation appropriate for association of the Ferroportin1 with test agent and substrate. For example, conditions under which an agent is assessed, such as media and temperature requirements, can initially be similar to those necessary for transport of iron substrate across the plasma membrane. One of ordinary skill in the art will know how to vary experimental conditions depending upon the biochemical nature of the test agent. The test agent can be added to the cells before or after the addition of an iron substrate. The concentration at which the test agent can be evaluated can be varied, as appropriate, to test for an increased effect with increasing concentrations.

Test agents to be assessed for their effects on iron transport can be any chemical (element, molecule, compound), made synthetically, made by recombinant techniques or isolated from a natural source. For example, test agents can be peptides, polypeptides, peptoids, sugars, hormones, or nucleic acid molecules, such as antisense nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates of cells, bacterial, animal or plant, or can be the cell lysates themselves. Presentation of test compounds to the test system can be in either an isolated form or as mixtures of compounds, especially in initial screening steps.

Thus, the invention relates to a method for identifying agents which alter iron export, the method comprising providing the test agent to the cell (wherein "cell" includes the plural, and can include cells of a cell strain, cell line or culture of primary cells or organ culture, for example), under conditions suitable for binding to its target, whether to the Ferroportin1 itself or to another target on or in the cell, wherein the cell comprises a Ferroportin1.

The cells to be tested for the effect of an agent on iron export can be "loaded" with iron by incubation of the cells with iron under conditions appropriate for iron uptake. The cells can be, for example, cells of transformed cell lines such as HeLa or 293 cells, fibroblasts, transformed fibroblasts or oocytes of *Xenopus laevis* or another appropriate species. The cells can also be cells transfected with nucleic acid encoding Ferroportin1, such that the cell expresses the Ferroportin1 protein to be tested for the effect of an agent. The iron can be labeled to facilitate its detection, for example, with a radioactive isotope.

The cells so loaded with iron are then washed with buffer or medium sufficient to remove iron external to the cells. The cells can then be divided into two equal aliquots, or two aliquots of known cell numbers. To one aliquot is added the agent to be tested for its effect on iron transport. To the other aliquot is added a volume of buffer, medium, etc. equivalent to that in which the agent added to the first aliquot was dissolved. The two aliquots of cells are then kept under the same culture conditions for a period of time to allow for the export of iron. After this period, the cells of each aliquot are separated from their surrounding medium, for example by centrifugation, and, for isolation of the cell pellet, by one or more additional washing steps. The medium can be collected in each case, and aliquots of each can be assayed for exported iron. Where the iron is radioactively labeled, the medium can be tested for radioactivity, as by scintillation counting. Alternatively, the cells or aliquots of the cells can be collected after the period of time allowing for iron export, and the cells can be lysed to prepare a cell extract to be assayed for iron retained in the cells. Where the cells to which an agent was added retain more iron than the control cells not receiving agent, the agent is an inhibitor of iron export. Where the cells to which an agent was added retain less iron than the control cells, the agent is an enhancer of iron export. If the cell medium is assayed, where the cells receiving agent export less iron into the medium than the control cells, then the agent is an inhibitor of iron transport. If the cells receiving agent export more iron into the medium than the control cells, then the agent is an enhancer of iron transport.

An agent determined to be an inhibitor (or enhancer) of Ferroportin1 function, such as iron binding and/or iron export, can be administered to cells in culture, or in vivo, to a mammal (e.g. human) to inhibit (or enhance) Ferroportin1 function. Such an agent may be one that acts directly on the Ferroportin1 protein (for example, by binding) or can act on an intermediate in a biosynthetic pathway to produce Ferroportin1, such as transcription of the ferroportin1 gene, processing of the mRNA, or translation of the mRNA. An example of such an agent is antisense oligonucleotide.

Cell-free assays can also be used to measure the transport of iron across a membrane, and therefor also to assess a test treatment or test agent for its effect on the rate or extent of iron transport. Isolated Ferroportin1, for example in the presence of a detergent that preserves the native 3-dimensional structure of the Ferroportin1 protein, or partially purified Ferroportin1 protein, can be used in an artificial membrane system typically used to preserve the native conformation and activity of membrane proteins. Such systems include liposomes, artificial bilayers of phospholipids, isolated plasma membrane such as cell membrane fragments, cell membrane fractions, or cell membrane vesicles, and other systems in which the Ferroportin1 protein can be properly oriented within the membrane to have transport activity. Assays for transport activity can be performed using methods analogous to those that can be used in cells expressing a Ferroportin1 protein whose function is to be measured. A labeled (e.g., radioactively labeled) iron substrate can be incubated on one side of a bilayer or in a suspension of liposomes constructed to integrate a properly oriented Ferroportin1 protein. The accumulation of iron with time can be measured, using appropriate means to detect the label (e.g., scintillation counting of medium on each side of the bilayer, or of the contents of liposomes versus the surrounding medium). Assays such as these can be adapted to use for the testing of agents which might interact with the Ferroportin1 to produce an inhibitory or an enhancing effect on the rate or extent of iron transport. That is, the above-described assay can be done in the presence or absence of the agent to be tested, and the results compared.

For examples of isolation of membrane proteins (ADP/ATP carrier and uncoupling protein), reconstitution into phospholipid vesicles, and assays of transport, see Klingenberg, M. et al., *Methods Enzymol.* 260:369-389 (1995). For an example of a membrane protein (phosphate carrier of *Saccharomyces cerevisiae*) that was purified and solubilized from *E. coli* inclusion bodies, see Schroer, A. et al., *J. Biol. Chem.* 273:14269-14276 (1998). The Glut1 glucose transporter of rat has been expressed in yeast. A crude membrane fraction of the yeast was prepared and reconstituted with soybean phospholipids into liposomes. Glucose transport activity could be measured in the liposomes (Kasahara, T. and Kasahara, M., *J. Biol. Chem.* 273:29113-29117 (1998)). Similar methods can be applied to the proteins and polypeptides of the invention.

Another embodiment of the invention is a method for inhibiting iron export in Ferroportin1-expressing cells of a mammal (e.g., a human), comprising administering to the mammal a therapeutically effective amount of an inhibitor of the transport function of Ferroportin1, thereby decreasing iron in the circulation. Hemochromatosis can be due to the inheritance of a mutant gene or due to secondary iron overload from an iron-loading anemia such as thalassemia or sideroblastic anemia. Where it is desirable to reduce the uptake of iron into the circulatory system through the intestine, for example, in the treatment of hemochromatosis in a human, one or more inhibitors of Ferroportin1 can be administered in an effective dose, and by an effective route, for example, orally, or by an indwelling device that can deliver doses to the small intestine. The inhibitor can be one identified by methods described herein, or can be one that is, for instance, structurally related to an inhibitor identified by methods described herein (e.g., having chemical adducts to better stabilize or solubilize the inhibitor). The invention further relates to compositions comprising inhibitors of iron uptake in a mammal, which may further comprise pharmaceutical carriers suitable for administration to a subject mammal, such as sterile solubilizing or emulsifying agents.

A further embodiment of the present invention is a method of enhancing or increasing iron uptake into the body, such as enhancing or increasing iron uptake in the small intestine (e.g., to treat a malabsorption syndrome or anemia). In this embodiment, a therapeutically effective amount of an enhancer of the transport function of Ferroportin1 can be administered to a mammalian subject, with the result that iron uptake in the small intestine is enhanced. In this embodiment, one or more enhancers of a Ferroportin1 protein is administered in an effective dose and by a route (e.g., orally or by a device, such as an indwelling catheter or other device) which can deliver doses to the gut. The enhancer of Ferroportin1 function can be identified by methods described herein or can be one that is structurally similar to an enhancer identified by methods described herein.

The invention further relates to antibodies that bind to an isolated or recombinant Ferroportin1, including portions of antibodies, which can specifically recognize and bind to one or more Ferroportin1 proteins. The antibodies and portions thereof of the invention include those which bind to Ferroportin1 proteins of zebrafish, or Ferroportin1 proteins of mouse or other mammalian species. In a specific embodiment, the antibodies bind to a naturally occurring Ferroportin1 of humans. The antibodies can be used in various methods to detect or to purify a protein of the present invention or a portion thereof such as ELISA, western blotting or immunoaffinity chromatography, to inhibit the function of a protein in a method of therapy, or to selectively inactivate an active site, or to study other aspects of the structure of these proteins, for example.

The antibodies of the present invention can be polyclonal or monoclonal. The term antibody is intended to encompass both polyclonal and monoclonal antibodies. Antibodies of the present invention can be raised against an appropriate immunogen, including proteins or polypeptides of the present invention, such as an isolated or recombinant Ferroportin1 or portions thereof, or synthetic molecules, such as synthetic peptides (e.g., conjugated to a suitable carrier). Preferred embodiments are antibodies that bind to any of the following, and which may cross-react with Ferroportin1 proteins of several species: zebrafish Ferroportin1, mouse Ferroportin1, or human Ferroportin1. The immunogen can be a polypeptide comprising a portion of a Ferroportin1 and having at least one function of a Ferroportin1, as described herein. To produce polyclonal antibodies, the immunogen is introduced into an animal that is not the original source of the immunogen (e.g., mouse Ferroportin1 or a fragment thereof injected into a non-murine animal).

The term antibody is also intended to encompass single chain antibodies, chimeric, humanized or primatized (CDR-grafted) antibodies and the like, as well as chimeric or CDR-grafted single chain antibodies, comprising portions from more than one species. For example, the chimeric antibodies can comprise portions of proteins derived from two different species, joined together chemically by conventional techniques or prepared as a single contiguous protein using genetic engineering techniques (e.g., DNA encoding the protein portions of the chimeric antibody can be expressed to produce a contiguous protein chain. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., U.S. Pat. No. 5,585,089; and Queen et al., European Patent No. EP 0 451 216 B1. See also, Newman, R. et al., *BioTechnology*, 10:1455-1460 (1992), regarding primatized antibody, and Ladner et al., U.S. Pat. No. 4,946,778 and Bird, R. E. et al., *Science*, 242:423-426 (1988) regarding single chain antibodies.)

Whole antibodies and biologically functional fragments thereof are also encompassed by the term antibody. Biologically functional antibody fragments which can be used include those fragments sufficient for binding of the antibody fragment to a Ferroportin1 to occur, such as Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Preparation of immunizing antigen (for instance, whole cells comprising a Ferroportin1 on the cell surface, or a purified Ferroportin1), and polyclonal and monoclonal antibody production can be performed using any suitable technique. A variety of methods have been described for the production of antibodies (See e.g., Kohler et al., *Nature*, 256:495-497 (1975) and *Eur. J. Immunol.* 6: 511-519 (1976); Milstein et al., *Nature* 266:550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); Chapter 11 In *Current Protocols In Molecular Biology*, Vol. 2 (containing supplements up through Supplement 49, 2000), Ausubel, F. M. et al., eds., John Wiley & Sons: New York, N.Y.). Generally, a hybridoma can be produced by fusing a suitable immortal cell line (e.g., a myeloma cell line such as SP2/0) with antibody producing cells. The antibody producing cells, preferably those obtained from the spleen or lymph nodes, can be obtained from animals immunized with the antigen of interest. Immunization of animals can be, for instance, by introduction of whole cells comprising Ferroportin1 protein on the cell surface. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies (including human antibodies) of the requisite specificity can used, including, for example, methods which select recombinant antibody from a library (e.g., Hoogenboom et al., WO 93/06213; Hoogenboom et al., U.S. Pat. No. 5,565,332; WO 94/13804, published Jun. 23, 1994; and Dower, W. J. et al., U.S. Pat. No. 5,427,908), or which rely upon immunization of transgenic animals (e.g., mice) capable of producing a full repertoire of human antibodies (see e.g., Jakobovits et al., *Proc. Natl. Acad. Sci. USA*, 90: 2551-2555 (1993); Jakobovits et al., *Nature*, 362:255-258 (1993); Lonberg et al., U.S. Pat. No. 5,569,825; Lonberg et al., U.S. Pat. No. 5,545,806; Surani et al., U.S. Pat. No. 5,545,807; and Kucherlapati, R. et al., European Patent No. EP 0 463 151 B1).

The invention also relates to compositions comprising a modulator of Ferroportin1 function. The term "modulate" as used herein refers to the ability of a molecule to alter the function of another molecule. Thus, modulate could mean, for example, inhibit, antagonize, agonize, upregulate, downregulate, induce, or suppress. A modulator has the capability of altering function of its target. Such alteration can be accomplished at any stage of the transcription, translation, expression or function of the protein, so that, for example, modulation of a target gene can be accomplished by modulation of the DNA or RNA encoding the protein, and the protein itself.

Antagonists or agonists (inhibitors or enhancers) of the Ferroportin1 proteins of the invention, antibodies that bind a Ferroportin1, or mimetics of a Ferroportin1 or of portions of a Ferroportin1 can be employed in combination with a non-sterile or sterile carrier or carriers for use with cells, tissues or organisms, such as a pharmaceutical carrier suitable for administration to a mammalian subject. Such compositions comprise, for instance, a media additive or a therapeutically effective amount of an inhibitor or enhancer compound to be identified by an assay of the invention and a pharmaceutically acceptable carrier or excipient. Such carriers may include, but are not limited to, saline, buffered saline, dextrose, water, ethanol, surfactants, such as glycerol, excipients such as lactose and combinations thereof. The formulation can be chosen by one of ordinary skill in the art to suit the mode of administration. The chosen route of administration will be influenced by the predominant tissue or organ location of the Ferroportin1 wherein it is intended that function is to be inhibited or enhanced. For example, for affecting the function of ferroportin1 in the duodenum, a particular administration can be oral or through a tube inserted into the stomach (e.g., direct stomach tube or nasopharyngeal tube), or through other means to accomplish delivery to the small intestine. The invention further relates to diagnostic and pharmaceutical packs and kits comprising one or more containers filled with one or more of the ingredients of the aforementioned compositions of the invention.

Compounds of the invention which are Ferroportin1 proteins, Ferroportin1 fusion proteins, Ferroportin1 mimetics, ferroportin1 gene-specific antisense poly- or oligonucleotides, inhibitors or enhancers of a Ferroportin1 may be employed alone or in conjunction with other compounds, such as therapeutic compounds. The pharmaceutical compositions may be administered in any effective, convenient manner, including administration by topical, oral, anal, vaginal, intravenous, intraperitoneal, intramuscular, subcutaneous, intranasal, transdermal or intradermal routes, among others. In therapy or as a prophylactic, the active agent may be administered to an individual as an injectable composition, for example as a sterile aqueous dispersion, preferably isotonic.

Alternatively, the composition may be formulated for topical application, for example, in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions.

In addition, the amount of the compound will vary depending on the size, age, body weight, general health, sex, and diet of the recipient of the compound, and the time of administration, the biological half-life of the compound, and the particular characteristics and symptoms of the disorder to be treated. Adjustment and manipulation of established dose ranges are well within the ability of those of skill in the art.

A further aspect of the invention is a method to identify a polymorphism, or the presence of an alternative or variant allele of a gene in the genome of an organism (of interest here, genes encoding Ferroportin1 proteins). As used herein, polymorphism refers to the occurrence of two or more genetically determined alternative sequences or alleles in a population. A polymorphic locus may be as small as a base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified alleleic form, or the most frequently occurring form can be arbitrarily designated as the reference (usually, "wildtype") form, and other allelic forms are designated as alternative (sometimes, "mutant" or "variant"). Diploid organisms may be homozygous or heterozygous for allelic forms.

An "allele" or "allelic sequence" is an alternative form of a gene which may result from at least one mutation in the nucleotide sequence. Alleles may result in altered mRNAs or polypeptides whose structure or function may or may not be altered. Any given gene may have none, one, or many allelic forms (polymorphism). Common mutational changes which give rise to alleles are generally ascribed to natural deletions, additions, or substitutions of nucleotides. Each of these types of changes may occur alone, or in combination with the others, one or more times in a given sequence.

Several different types of polymorphisms have been reported. A restriction fragment length polymorphism (RFLP) is a variation in DNA sequence that alters the length of a restriction fragment (Botstein et al., *Am. J. Hum. Genet.* 32:314-331 (1980)). The restriction fragment length polymorphism may create or delete a restriction site, thus changing the length of the restriction fragment. RFLPs have been widely used in human and animal genetic analyses (see WO 90/13668; WO 90/11369; Donis-Keller, *Cell* 51:319-337 (1987); Lander et al., *Genetics* 121:85-99 (1989)). When a heritable trait can be linked to a particular RFLP, the presence of the RFLP in an individual can be used to predict the likelihood that the individual will also exhibit the trait.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., *FEBS Lett.* 307:113-115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs (short tandem repeats) and VNTRs (variable number tandem repeats). Some single nucleotide polymorphisms occur in protein-coding sequences, in which case, one of the polymorphic forms may give rise to the expression of a defective or other variant protein and, potentially, a genetic disease. Other single nucleotide polymorphisms occur in noncoding regions. Some of these polymorphisms may also result in defective protein expression (e.g., as a result of defective splicing). Other single nucleotide polymorphisms have no phenotypic effects.

Many of the methods described below require amplification of DNA from target samples and purification of the amplified products. This can be accomplished by PCR, for instance. See generally, *PCR Technology, Principles and Applications for DNA Amplification* (ed. H. A. Erlich), Freeman Press, New York, N.Y., 1992; *PCR Protocols: A Guide to Methods and Applications* (eds. Innis, et al.), Academic Press, San Diego, Calif., 1990; Mattila et al., *Nucleic Acids Res.* 19:4967 (1991); Eckert et al., *PCR Methods and Applications* 1:17 (1991); *PCR* (eds. McPherson et al., IRS Press, Oxford); and U.S. Pat. No. 4,683,202.

Other suitable amplification methods include the ligase chain reaction (LCR) (see Wu and Wallace, *Genomics* 4:560 (1989); Landegren et al., *Science* 241:1077 (1988)), transcription amplification (Kwoh et al., *Proc. Natl. Acad. Sci. USA* 86:1173 (1989), self-sustained sequence replication (Guatelli et al., *Proc. Natl. Acad. Sci. USA* 87:1874 (1990), and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Another aspect of the invention is a method for detecting a variant allele of a human ferroportin1 gene, comprising preparing amplified, purified ferroportin1 DNA from a reference human and amplified, purified, ferroportin1 DNA from a "test" human to be compared to the reference as having a variant allele, using the same or comparable amplification procedures, and determining whether the reference DNA and test DNA differ in DNA sequence in the ferroportin1 gene, whether in a coding or a noncoding region, wherein, if the test DNA differs in sequence from the reference DNA, the test DNA comprises a variant allele of a human ferroportin1 gene. The following is a discussion of some of the methods by which it can be determined whether the reference ferroportin1 DNA and test ferroportin1 DNA differ in sequence.

Direct Sequencing. The direct analysis of the sequence of variant alleles of the present invention can be accomplished using either the dideoxy chain termination method or the Maxam and Gilbert method (see Sambrook et al., *Molecular Cloning. A Laboratory Manual*, 2nd ed., Cold Spring Harbor Press, New York 1989; Zyskind et al., *Recombinant DNA Laboratory Manual*, Acad. Press, 1988).

Denaturing Gradient Gel Electrophoresis. Amplification products generated using the polymerase chain reaction can be analyzed by the use of denaturing gradient gel electrophoresis. Different alleles can be identified based on the different sequence-dependent strand dissociation properties and electrophoretic migration of DNA in solution (chapter 7 in Erlich, ed. *PCR Technology, Principles and Applications for DNA Amplification*, W.H. Freeman and Co., New York, 1992).

Single-strand Conformation Polymorphism Analysis. Alleles of target sequences can be differentiated using single-strand conformation polymorphism analysis, which identifies base differences by alteration in electrophoretic migration of single stranded PCR products, as described in Orita et al., *Proc. Natl. Acad. Sci. USA* 86:2766-2770 (1989). Amplified PCR products can be generated as described above, and heated or otherwise denatured, to form single-stranded amplification products. Single-stranded nucleic acids may refold or form secondary structures which are partially dependent on the base sequence. The different electrophoretic mobilities of single-stranded amplification products can be related to base-sequence differences between alleles of target sequences.

Detection of Binding by Protein That Binds to Mismatches. Amplified DNA comprising the ferroportin1 gene or portion of the gene of interest from genomic DNA, for example, of a normal individual is prepared, using primers designed on the basis of the DNA sequences provided herein. Amplified DNA is also prepared, in a similar manner, from genomic DNA of an individual to be tested for bearing a distinguishable allele. The primers used in PCR carry different labels, for example, primer 1 with biotin, and primer 2 with $^{32}$P, Unused primers are separated from the PCR products, and the products are quantitated. The heteroduplexes are used in a mismatch detection assay using immobilized mismatch binding protein (MutS) bound to nitrocellulose. The presence of biotin-labeled DNA wherein mismatched regions are bound to the nitrocellulose via MutS protein, is detected by visualizing the binding of streptavidin to biotin. See WO 95/12689. MutS protein has also been used in the detection of point mutations in a gel-mobility-shift assay (Lishanski, A. et al., *Proc. Natl. Acad. Sci. USA* 91:2674-2678 (1994)).

Other methods, such as those described below, can be used to distinguish a ferroportin1 allele from a reference allele, once a particular allele has been characterized as to DNA sequence.

Allele-specific probes. The design and use of allele-specific probes for analyzing polymorphisms is described by e.g., Saiki et al., *Nature* 324:163-166 (1986); Dattagupta, EP 235,726, Saiki, WO 89/11548. Allele-specific probes can be designed so that they hybridize to a segment of a target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Allele-specific Primers. An allele-specific primer hybridizes to a site on target DNA overlapping a polymorphism, and only primes amplification of an allelic form to which the primer exhibits perfect complementarity. See Gibbs, *Nucleic Acid Res.* 17:2427-2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

Gene Chips. Allelic variants can also be identified by hybridization to nucleic acids immobilized on solid supports (gene chips), as described, for example, in WO 95/11995 and U.S. Pat. No. 5,143,854, both of which are incorporated herein by reference. WO 95/11995 describes subarrays that are optimized for detection of a characterized variant allele. Such a subarray contains probes designed to be complementary to a second reference sequence, which is an allelic variant of the first reference sequence.

EXAMPLES

Methods

Zebrafish Strains and Studies

Linkage analysis was performed on haploid or diploid embryos obtained from AB/DAR, AB/SJD or AB/WIK hybrids (Westerfield, M., *The Zebrafish Book*, Univ. Oregon Press, Eugene, 1993). Wright-Giemsa and o-dianisidine staining of embryos were performed as described (Ransom, D. G., et al., *Development,* 123:311-319, 1996). In situ hybridization analysis was performed as described (Thompson, M. A., et al., *Dev. Biol.,* 197:248-269, 1998).

Genetic Mapping and Genotyping and Library Screens

Linkage to centromeric markers (Knapik, E. W., et al., *Nature Genet.,* 18:338-343, 1998) was performed by half-tetrad analysis (Johnson, S. L., et al., *Genetics,* 139:1727-1735, 1995). For fine genetic mapping, haploids were genotyped on the proximal side of the locus with one of the following RAPD markers (Operon Technologies, Alemeda, Calif.); 4W1600, 6Q1300, or 4AC800, and on the distal side with the markers 4K1300 or 061020. Diploid mutant embryos were genotyped on the proximal side with the microsatellite markers z8505 or z9479 and on the distal side with z8363 (Shimoda, N., et al., *Genomics,* 58:219-232, 1999). Library screens were performed as described (Brownlie, A., et al., *Nature Genet.,* 20:244-250, 1998).

In situ hybridization and rescue experiment embryos (see below) were genotyped using allele specific oligonucleotide (ASO) hybridization assays specific to the $weh^{tp85c}$ and $weh^{th238}$ ferroportin1 alleles (Farr, C. J., et al., *Proc. Natl. Acad. Sci. USA,* 85:1629-1633, 1988; Wood, W. I., et al., *Proc. Natl. Acad. Sci. USA,* 82:1585-1588, 1985). The $weh^{th238}$ oligonucleotides were developed to distinguish the C to A mutation in the $weh^{th238}$ allele from the wild-type allele. Wild-type is 5'-AAAGAAGTGCGGCCTCATC-3'(SEQ ID NO:8) and mutant $weh^{th238}$ allele is 5'-AAAGAAGTGAGGCCTCATC-3'(SEQ ID NO: 9). The $weh^{tp85c}$ oligonucleotides were developed to distinguish the G to T mutation in the $weh^{tp85c}$ allele from wild-type.

```
Wild-type is
5'-GAGCAAATTGGCAGGTAAG-3'      (SEQ ID NO: 10)
and mutant weh^tp85c allele is
5'-GAGCAAATTTGCAGGTAAG -3'.    (SEQ ID NO: 11)
```

Isolation of the Mouse and Human Ferroportin1 cDNAs

EST clones were identified that contained the 5' end (GenBank accession # D632209) and 3' end (GenBank accession # W23461) of human ferroportin1 and the 3' end of mouse ferroportin1 (GenBank accession # AA500296). The coding region of human and mouse ferroportin1 cDNAs were cloned by RT-PCR with a forward primer made to the conserved iron response element (IRE) sequence in the 5' untranslated region (5'-CAACTTCAGCTACAGTGTTAG-3' (SEQ ID NO: 12)) and a reverse primer just 3' of the stop codon of each cDNA (mouse 5'-TTATACAACAGATGTATTCGGT-3' (SEQ ID NO:13) and human 5'-AACTGTCTCAAACAACAGATG-3' (SEQ ID NO: 14)).

Embryo Injection Experiments

A zebrafish Ferroportin1-GFP fusion protein construct was created by PCR. The forward PCR primer contained the start codon, 5'-CCGCTCGAGAACGCACAATGGACAGC-CCTG-3' (SEQ ID NO: 15). The reverse primer contained the last codon, 5'-CCGCTCGAGTACAGAGTTTGGAAGT-GAGGG-3' (SEQ ID NO: 16). The PCR product was subcloned into the GFP expression vector pEGFP-N1 (Clontech, Palo Alto, Calif.). Embryos from a cross of two $weh^{th238}$ heterozygotes were injected (Westerfield, M., *The Zebrafish Book*, Univ. Oregon Press, Eugene, 1993) with the ferroportin1-GFP plasmid (300 ng/ml). For the iron-dextran rescue experiment, 48 hr mutant embryos from a $weh^{tp85c}$ cross were injected intravenously with an iron-dextran solution (Sigma, 100 mg/ml).

*Xenopus* Oocyte Injections and [55]Fe Efflux Experiments cRNA for injection was prepared using the mMessage Machine kit (Ambion, Austin, Tex.), using a construct containing either the rat DMT1 cDNA in pSPORT1 (gift from Hiromi Gunshin (Gunshin, H., et al., *Nature,* 388:482-488, 1997)) or the zebrafish ferroportin1 cDNA in the vector pXT7 (kindly provided by Sergei Sokol). Defollicularized oocytes were incubated in ND96 (96 mM NaCl, 2 mM KCl, 1.8 mM $CaCl_2$, 1 mM $MgCl_2$, 5 mM Hepes, and 2.5 mM sodium pyruvate, pH 7.4) and injected with either 20 ng of DMT1 cRNA alone or 20 ng each of both the DMT1 and ferroportin1 cRNAs. $^{55}$Fe uptake and efflux were performed 48 hrs after injection. $^{55}$Fe uptake was performed in 500 µl of a solution containing 60 µM $^{55}$FeCl$_2$, 100 mM NaCl, 10 mM Hepes and 1 mM ascorbic acid at pH 5.5 for 30 minutes. $^{55}$Fe uptake was stopped by incubation of the oocytes in 1 mM cold FeCl$_2$, 100 mM NaCl, 10 mM Hepes, and 1 mM ascorbic acid at pH 6.0 for 30 minutes. Individual oocytes were placed in 500 µl of either efflux buffer (100 mM NaCl, 10 mM Hepes at pH 7.4) alone or efflux buffer containing a final concentration of 20 mg/ml apo-transferrin for 60 minutes. After incubation, the $^{55}$Fe levels of both the efflux solution and the individual oocytes lysed in 10% SDS were measured by scintillation counting.

Mouse In Situ Hybridization and Northern Blot Analysis

In situ hybridization of murine embryos was performed as described (Palis, J., et al., *Mol. Reprod. Dev.*, 42:19-27, 1995). An adult multi-tissue Human Northern blot (Clontech, Palo Alto Calif.) containing 2 µg of poly A$^+$ mRNA per lane was probed with a human ferroportin1 EST (GenBank accession # W05488). The mouse intestinal Northern blot containing 20 µg of total RNA per lane was probed with a mouse ferroportin1 EST (GenBank accession # AA500296).

Antibody Generation and Immunohistochemistry

A rabbit polyclonal antibody was generated to a peptide consisting of the C-terminal 19 amino acids of the human Ferroportin1 protein (Genemed Synthesis, San Francisco Calif.). Antiserum was affinity-purified against the peptide. Formalin or Bouin's fixed paraffin-embedded specimens were deparaffinized and heat treated for 30 min in 1.0 mM EDTA, pH 8.0, in a Black and Decker steamer (Model HS80). Endogenous peroxidase activity was quenched in methanol and 3% hydrogen peroxide (5:1, vol/vol). The slides were then incubated in 3% normal swine serum in 0.05 M Tris, pH 7.6, followed by rabbit anti-Ferroportin1 antibody (7 µg/ml), and sequentially in HRP-conjugated goat anti-rabbit immunoglobulins (1:40 dilution, Dako), HRP-conjugated rabbit anti-goat immunoglobulins (1:40 dilution, Dako), followed by HRP-conjugated swine anti-rabbit immunoglobulins (1:52 dilution, Dako), each prepared in 0.10 M Tris, pH 7.6, containing (4%) human AB serum. Antibody localization was determined using DAB in 0.5 M Tris (pH 7.6) containing (0.035%) hydrogen peroxide. Slides were counterstained with methyl green. Control samples were incubated with normal rabbit serum or purified rabbit immunoglobulins at a protein concentration equal to the antibody preparation. In addition, preincubation of the antibody with specific peptide at a 550-fold molar excess neutralized the reactivity.

Red Cell Iron Measurement

Iron levels in red blood cells were measured by Atomic Absorption Spectrometer Model 3030 equipped with Zeeman Graphite Furnace and Autosampler, (Perkin Elmer Corp.). A cell sample (at least 30,000 cells in 20 □l PBS) or blank (PBS) was diluted with 40 µl of 480 mg/dl of magnesium nitrate (matrix modifier); 20 µl of the mixture was injected into the instrument and analyzed in duplicate. The instrument was calibrated with iron standards of 10, 25, 100 and 250 ng/ml prepared from Atomic Spectroscopy Standard (Perkin Elmer Corp).

Structure Prediction

Hydropathy plots (Kyte-Doolittle) were obtained using the Genetics Computer Group (GCG) programs PEPTIDE-STRUCTURE and PEPPLOT with an hydropathy window of 14. Transmembrane amino acid segments were identified and their topography predicted using the programs PHDhtm (www.embl-heidelberg.de/predictprotein/predictprotein.html), HMMTOP (www.enzim.hu/hmmtop/), TMHMM (www.cbs.dtu.dk/services/TMHMM-1.0/), TMpred (www.ch.embnet.org/software/TMPRED_form.html), TopPred2 (www.biokemi.su.se/~server/toppred2/), and SOSUI (www.tuat.ac.jp/~mitaku/). Most analyses predict 10 ™ segments. Some predict that the first and last TM segments are split, and that Ferroportin contains 12 segments. Others predict that TM segments 4 and are not split and only 9 segments are present.

Example 1

Observations on Weissherbst Zebrafish Mutants

Two independent autosomal recessive mutations of the zebrafish hypochromic blood mutant weissherbst (weh), weh$^{th238}$ and weh$^{tp85c}$, were isolated as part of a large-scale screen for ethyl nitroso urea (ENU) induced mutations that disrupt embryonic development in zebrafish (Haffter, P., et al., *Danio rerio. Development*, 123:1-36, 1996). These weh mutants were identified in a morphologic screen for defects in circulating erythroid cells (Ransom, D. G., et al., *Development*, 123:311-319, 1996). While the number of circulating erythroid cells of both mutant alleles are normal at 33 and 48 hours post fertilization (hpf), the weh mutant cells are hypochromic (lacking red color). Mutant embryos show little, if any, hemoglobin compared to wild-types at 33 hpf and 48 hpf (by o-dianisidine staining), but some hemoglobin is detectable at 72 hpf. The weh$^{th238}$ allele has less o-dianisidine staining compared to the weh$^{tp85c}$ allele at 72 hpf, suggesting that it is a more severely defective allele. In addition to the hypochromia, a progressive decrease in red cell number occurs after 48 hpf. By 96 hpf, the number of circulating erythroid cells in mutants decreases to approximately 20% of the number in wild-type. The weh mutant cells at days 2 (56 hpf) and 3 (80 hpf) have a large nucleus and basophilic cytoplasm characteristic of more immature erythroid cells, and on day 5 (125 hpf) the remaining mutant cells are misshapen. Further studies of erythroid differentiation reveal that embryonic globin mRNA levels are abnormally maintained during maturation. Although weh mutants have no gross organ defects in addition to their anemia, all mutant embryos die between day 7 and day 14 of development.

Given the possibility that hypochromia could result from iron deficiency, we measured iron levels in weh erythroid cells. The level of iron measured in 10$^4$ wild-type cells ranged from 0.093 ng to 0.208 ng (n=3), whereas the levels of iron in the same number of weh mutant cells ranged from 0.014 ng to 0.033 ng (n=3). The 4-9 fold decrease in erythrocyte iron levels could be due to low levels of iron in circulation. As confirmation of this hypothesis, iron-dextran injected intravenously into weh$^{tp85c}$ mutant embryos was shown to completely rescue hemoglobin production as seen by o-dianisidine staining of hemoglobin. This rescue demonstrated that weh mutant erythroid cells are fully capable of hemoglobinization, and that the hypochromia is caused by inadequate circulatory iron levels.

Example 2

Isolation of weh Mutant Gene

To gain further insight into this phenotype, we isolated the weh mutant gene by positional cloning methods. Study of the segregation of centromeric microsatellite markers in half-tetrad gynogenetic diploid embryos localized weh to linkage group 9. Genetic mapping placed the weh locus in an approximately 6 cM interval between the random amplified polymorphic DNA (RAPD) markers 4K1300 and 6Q1300 (FIG. 1).

We isolated more closely linked markers using amplified fragment length polymorphism (AFLP) analysis (Ransom, D. G., et al., pp. 195-210 in *The Zebrafish: Genetics and Genomics*, eds. Detrich, H. W. L., Westerfield, M. & Zon, L. I., Academic, San Diego, 1999; Vos. P., et al., *Nucleic Acids Res.*, 23:4407-4414, 1995), scanning approximately 10,000 polymorphic loci. Single strand conformational polymorphism (SSCP) analysis showed that the AFLP marker 136 was 0.13 cM proximal to the weh locus (FIG. 1).

A chromosomal walk towards the gene was initiated from the 136 marker (FIG. 1), resulting in the identification of a critical interval that contained the weh gene (FIG. 1). In an attempt to identify potential candidates for the weh gene, we used a hybridization strategy to screen cDNA libraries for genes located on the PAC clones identified in the region of the weh locus. We hybridized a radiolabelled insert of PAC clone 170G3 to zebrafish gridded cDNA libraries. Screening of 100,000 gridded cDNA clones identified 5 clones of a novel cDNA, designated WC1 for weh cDNA #1. Analysis of WC1 mRNA expression in embryos and sequencing WC1 from weh$^{th238}$ mutants suggested that WC1 was not a candidate for weh. Two genes, STAT1 and glutaminase, were isolated by hybridization of the zebrafish PAC clone 87I4 (FIG. 1) to gridded cDNA libraries. The human orthologs of WC1, STAT1 and glutaminase are localized to human chromosome 2 in a 2.4 cM interval, demonstrating conserved chromosomal synteny among vertebrates (Postlethwait, J. H., et al., *Nature Genet.*, 18:345-349, 1998). Homology searches identified a pufferfish (*Fugu rubripes*) cosmid clone (121D21) that contained both WC1 and STAT1. This cosmid also contained *Fugu* homologs of other genes located on human chromosome 2. Using primers designed to the pufferfish sequence of one of these genes (121D21 aB3), a 200 bp fragment of the zebrafish ortholog was amplified from PAC 211013. A full length cDNA (3.7 kb) of this gene, hereafter referred to as ferroportin1, was isolated from a zebrafish kidney cDNA library.

Figure 2B:
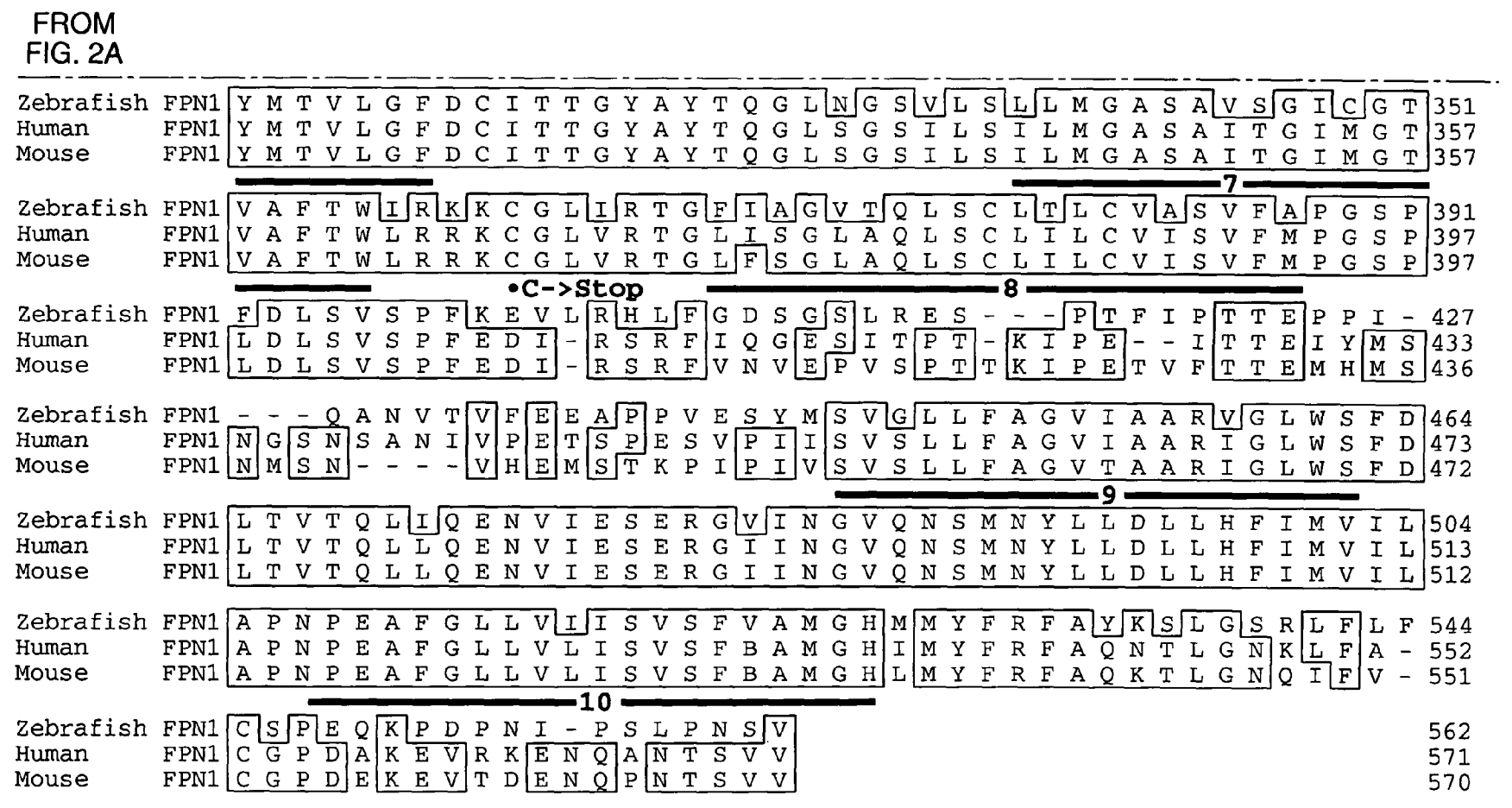

This gene, ferroportin1, has a predicted open reading frame of 562 amino acids (FIG. 2). Sequence analysis of the weh$^{th238}$ allele identified a C to A nucleotide transversion that causes premature termination of translation at codon 361 (FIG. 2). Similar analysis of the weh$^{tp85c}$ allele identified a single amino acid change, Leu168Phe, resulting from a G to T nucleotide difference (FIG. 2). The finding of a premature stop mutation in weh$^{th238}$ strongly suggests that the weh mutant phenotype is caused by a defect in ferroportin1. Mouse and human ferroportin1 cDNA clones were obtained by RT-PCR of RNA isolated from liver and placenta, respectively. A conserved sequence, predicted to form a hairpin loop structure typical of iron response elements (IREs) (Eisenstein, R. S., et al., *J. Nutr.*, 128:2295-2298, 1998), was identified in the 5' untranslated region (UTR) of the cDNAs from all three species. Based on protein structure prediction analysis, Ferroportin1 contains at least 10 transmembrane segments (FIG. 2).

Example 3

Expression of Ferroportin1

In situ hybridization analysis of zebrafish embryos shows that ferroportin1 mRNA is not expressed in erythroid cells. Ferroportin1 mRNA is detected at 18 hpf through 48 hpf in the yolk syncytial layer (YSL). The YSL is the peripheral layer of the yolk cell that lies just below the membrane (Kimmel, C. B., et al., *Dev. Dyn.*, 203:253-310, 1995). This layer surrounds the entire yolk of the embryo and consists of yolk-free cytoplasm and nuclei. Yolk has been shown to contain nutrients needed during development (Richards, M. P., *Poult. Sci.*, 76:152-164, 1997), including iron (Richards, M. P., *Poult. Sci.*, 76:152-164, 1997; Dumont, J. N., *J. Exp. Zool.*, 204:193-217, 1978; Craik, J. C., *Comp. Biochem. Physiol. A.*, 83:515-517, 1986). Embryos express ferroportin1 in the region of the YSL at 18 hpf that lies just below the developing hematopoietic cells in the intermediate cell mass (Al-Adhami, M. A., et al., *Develop. Growth Differ.*, 19:171-179, 1977). At 48 hpf, ferroportin1 is expressed in the brain and in a localized region of the YSL. Note that expression is in the same region of the YSL over which the blood flows (Reib, J. P., *Annales D'Embryologie et de Morphogenese*, 6:43-54, 1973). At both time-points, ferroportin1 is expressed in the region of the YSL adjacent to the blood, but not by the entire YSL. This pattern of expression suggests that ferroportin1 expression and function in the YSL is linked to red blood cell development. Considering the iron-dextran rescue of hemoglobin production in weh mutants, the YSL expression of ferroportin1 suggested that the gene might function in the transport of iron from the yolk to the embryonic circulation.

To provide evidence that defects in the ferroportin1 gene cause the weh mutant phenotype, we injected a plasmid that expresses Ferroportin1 fused to green fluorescent protein (GFP) into the yolk cell between the 256 and 1000 cell stages (Kimmel, C. B., et al., *Dev. Dyn.*, 203:253-310, 1995). At 48 hours of development, 33% of injected embryos expressed GFP strictly in the YSL. At 80 hpf, the phenotype of mutant embryos expressing GFP was compared to the uninjected mutants. The Ferroportin1-GFP-expressing mutant embryos (n=9) had considerably more hemoglobin expression than uninjected mutants as observed by o-dianisidine staining. This partial rescue of the hypochromia provides further evidence that ferroportin1 is the weh gene, and demonstrates that Ferroportin1 acts in the YSL. The rescue of the weh mutant phenotype by intravenous iron-dextran injection and by Ferroportin1 expressed in the YSL indicates that Ferroportin1 functions to deliver yolk iron into the embryonic circulation.

Figure 3:
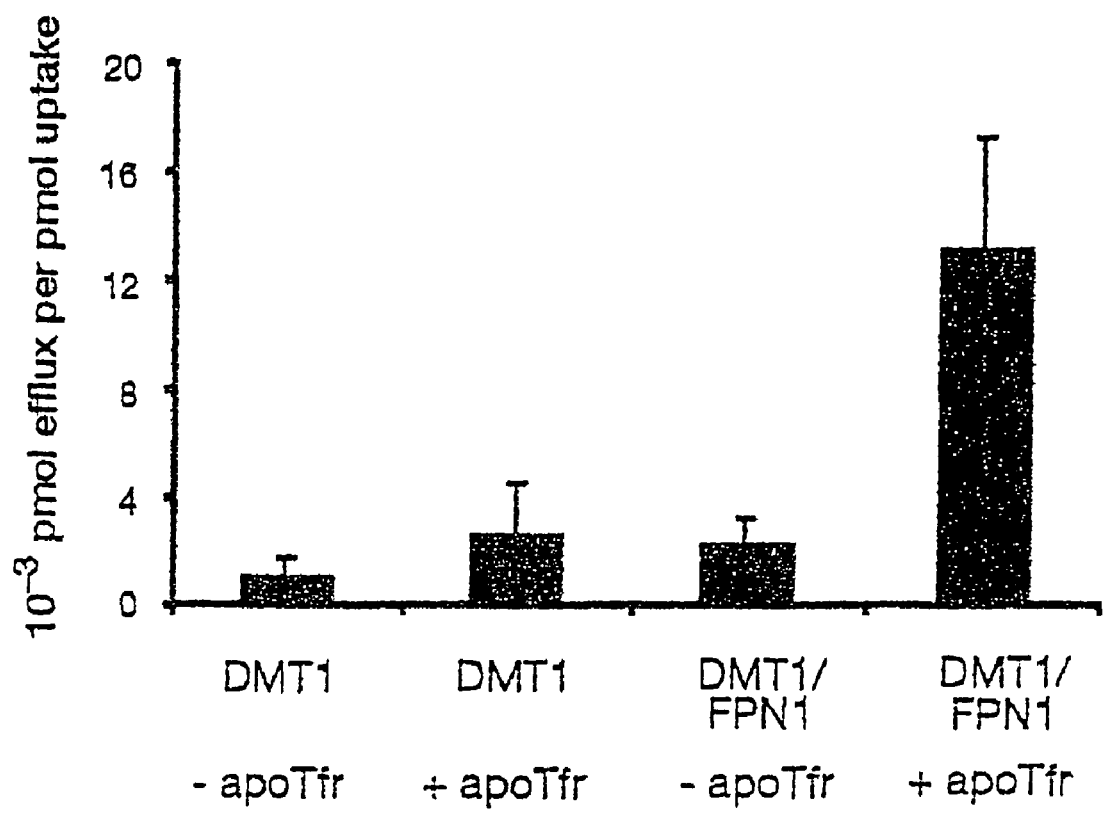
FIG. 3 is a bar graph showing the measurement of iron efflux from *Xenopus* oocytes. Oocytes expressing either DMT1 alone or DMT1 and FPN1 were loaded with $^{55}$Fe by incubation in uptake buffer containing 60 µM $^{55}$FeCl$_2$. Efflux from individual oocytes was measured by incubation of oocytes in 500 µl of efflux buffer with or without 20 mg/ml apo-transferrin (−apoTfr and +apoTfr). After efflux, the total $^{55}$Fe content of both the efflux solution and the individual oocytes was measured by scintillation counting. The data are expressed as an average (n=6) of the ratio of the pmols of efflux to the pmols of uptake per oocyte.

The function of Ferroportin1 was tested using a *Xenopus* oocyte expression system. Since the proposed function of Ferroportin1 is to export iron, it was necessary to first load the oocytes with $^{55}$Fe. Radioactive iron loading was accomplished through the expression of the iron transporter DMT1 in oocytes and then loading of $^{55}$Fe at pH 5.5. $^{55}$Fe loaded oocytes that expressed either DMT1 alone, or DMT1 and Ferroportin1, were tested for iron export activity either in the presence or absence of apo-transferrin, an iron chelator. To normalize for the iron content in each individual oocyte, the ratio of efflux to uptake was calculated. Our results showed that, in the presence of apo-transferrin, the efflux to uptake ratio in oocytes expressing Ferroportin1 was five fold greater than control oocytes not expressing Ferroportin1 (FIG. 3, P<<0.001).

Example 4

Expression of Ferroportin1 in Embryonic and Adult Tissues of Mammals

To evaluate a potential role for ferroportin1 in iron transport in mammals, we examined tissue expression. Northern blot analysis showed highest levels of expression in human placenta, liver, spleen, and kidney. In mice, ferroportin1 mRNA is expressed specifically in the duodenum but not in the jejunum or ileum. Additionally, ferroportin1 is expressed in the large intestine. Most intestinal iron absorption occurs in the proximal duodenum, placing ferroportin1 in a physiologically appropriate location to play a role in intestinal iron absorption. mRNA in situ hybridization analysis was performed on sections of mouse embryos. The primitive erythroblasts derived from the blood islands do not express ferroportin1, whereas the trophoblast cells of the inner placenta express high levels of ferroportin1 RNA. Ferroportin1 transcripts were found in the inner placenta (labyrinth zone) and the trophoblast giant cells at the border between the outer placenta (spongiotrophoblast), but not in the maternal deciduum. Ferroportin1 expression is also present in the visceral endoderm of the yolk sac surrounding the embryo proper. Within the embryo proper, ferroportin1 transcripts were detected in several tissues, including the vascular plexus surrounding the central nervous systems, but particularly the gut and liver. The expression of ferroportin1 in placenta, duodenum, and liver, all prominent sites of iron transport, is consistent with the proposed role of the gene in iron transport.

In order to characterize the expression of Ferroportin1 protein, we generated a specific rabbit polyclonal antibody against a Ferroportin1 peptide. In the human placenta, Ferroportin1 protein was primarily expressed in a basal location within the syncytiotrophoblasts. The basal surface of the syncytiotrophoblast interfaces with the fetal circulation, whereas the apical surface contacts the maternal circulation. The mammalian placenta and the zebrafish YSL provide a homologous function, serving as the site of iron transfer between mother and embryo. Taken together with the functional data in zebrafish and *Xenopus*, Ferroportin1 is likely to export iron from the syncytiotrophoblast into the embryonic circulation.

A similar analysis of mouse duodenum showed Ferroportin1 staining in enterocytes in the villus. The intensity of staining was stronger at the tip of the villus compared to the crypt. Staining was particularly strong at the basolateral surface of the enterocyte. The duodenal enterocytes of the small intestine are polarized epithelial cells that transport iron into the intestinal capillaries through the basolateral membrane. The mechanism of intestinal basolateral iron transport has not been established. Sex-linked anemia (sla) mice have a defect in basolateral iron transport in the duodenum, based on ferrokinetic studies and the presence of abnormal iron deposits in duodenal enterocytes (Bannerman, R. M., *Fed. Proc.,* 35:2281-2285, 1976). Analogous to weh mutants, the sla mouse has a defect in transport of maternal iron to the embryonic circulation (Kingston, P. J., et al., *Br. J. Haematol.,* 40:265-276, 1978). The sla phenotype is due to a mutation in the membrane-bound multi-copper ferroxidase gene, hephaestin (Vulpe, C. D., et al., *Nature Genet.,* 21:195-199, 1999). In *Saccharomyces cerevisiae*, the hephaestin-like ferroxidase FET3 is required for high affinity iron uptake by the iron transporter FTR1 (Askwith, C., et al., *Cell,* 76:403-410, 1994; Stearman, R., et al., *Science,* 271:1552-1557, 1996). Expression of Ferroportin1 at the basolateral surface of duodenal enterocytes in mouse and the multiple-transmembrane structure of the protein make it an excellent candidate to function as a basolateral iron transporter.

Additional data from the weh mutant suggests that Ferroportin1 functions in the intestine of the adult zebrafish. Both in situ hybridization studies and immunohistochemistry showed expression of zebrafish ferroportin1 in the intestine. In addition, iron-dextran rescued mutant embryos live past the normal time of lethality (day 7-14). We have successfully raised these rescued embryos to adulthood. These fish are smaller than their wildtype siblings and have a profound hypochromic anemia. Since these fish eat a normal diet replete in iron, but nonetheless are severely anemic, these data suggest that the gene is required for intestinal iron absorption in addition to yolk sac transport. Based on the basolateral expression pattern of Ferroportin1 in mammalian enterocytes and the implication that ferroportin1 is required for intestinal iron transport in zebrafish, it is likely that the protein is involved in iron export from enterocytes in mammals. Further experiments are required to determine whether Ferroportin1 cooperates with hephaestin in these cells.

Other tissues may utilize ferroportin1 as an iron exporter. Very high levels of expression are evident in Kupffer cells of human liver, the resident macrophages of the liver, and macrophages located within the splenic red pulp. Hepatocytes were also positive by immunohistochemical staining. Ferroportin1 could play a role in iron export from macrophages, a critical function in recycling of iron from senescent erythrocytes.

While this invention has been particularly shown and described with references to example embodiments thereof, it will be understood by those skilled in the art that various changes in form and details may be made therein without departing from the scope of the invention encompassed by the appended claims.

What is claimed is:

1. An isolated polypeptide comprising the amino acid sequence of SEQ ID NO:2, SEQ ID NO:4, or SEQ ID NO:6.

* * * * *

SEQUENCE LISTING

```
<160> NUMBER OF SEQ ID NOS: 16

<210> SEQ ID NO 1
<211> LENGTH: 3773
<212> TYPE: DNA
<213> ORGANISM: Danio rerio
<220> FEATURE:
<221> NAME/KEY: CDS
<222> LOCATION: (238)...(1926)

<400> SEQUENCE: 1
acgaggtgcg agcggctctg gccatttcgg gaattatatg tttttattca catagttgtt      60
ctagaaaggt tatttctctc cgacttcagc tacagtgata gctaagtttg gagaggagaa     120
aagggagata ttcgtgattt gcgcaggaat atatttgcag cgaggattta ctttgcccga     180
gccttacaaa ggagttcaaa tcccggcgag aaaaaaacaa tcgataaaaa acgcaca atg    240
                                                                 Met
                                                                   1
```

```
gac agc cct gca tca aag aaa cct cgc tgt gag agg ttc cgc gaa ttc      288
Asp Ser Pro Ala Ser Lys Lys Pro Arg Cys Glu Arg Phe Arg Glu Phe
          5                  10                  15 ttc aag tct gca aaa ttc ctc att tac gtc gga cat gcc ctc tcg aca      336
Phe Lys Ser Ala Lys Phe Leu Ile Tyr Val Gly His Ala Leu Ser Thr
         20                  25                  30 tgg ggg gat cgg atg tgg aat ttt gct gtg gct gtg ttt ctg gtg gag      384
Trp Gly Asp Arg Met Trp Asn Phe Ala Val Ala Val Phe Leu Val Glu
     35                  40                  45 ctg tat ggc aat agt tta ctc ctg aca gcc gtg tat gga ctg gtg gtc      432
Leu Tyr Gly Asn Ser Leu Leu Leu Thr Ala Val Tyr Gly Leu Val Val
 50                  55                  60                  65 gcg ggc tcc gtg ctc tta ctg ggc gct att att ggt gac tgg gtt gac      480
Ala Gly Ser Val Leu Leu Leu Gly Ala Ile Ile Gly Asp Trp Val Asp
             70                  75                  80 aaa aac ccc aga ttg aaa gtg gca cag acg tct ttg gtt gtc cag aac      528
Lys Asn Pro Arg Leu Lys Val Ala Gln Thr Ser Leu Val Val Gln Asn
                 85                  90                  95 agt gct gtc att ctc tgt ggt gcc ctt ttg atg gct gtt ttc cag ttc      576
Ser Ala Val Ile Leu Cys Gly Ala Leu Leu Met Ala Val Phe Gln Phe
            100                 105                 110 aaa caa cag ctt tct agc atg tat gat gga tgg ttg ctg aca aca tgc      624
Lys Gln Gln Leu Ser Ser Met Tyr Asp Gly Trp Leu Leu Thr Thr Cys
        115                 120                 125 tac ata atg gtc atc tcc att gct aat atc gct aac ctg gcc agc aca      672
Tyr Ile Met Val Ile Ser Ile Ala Asn Ile Ala Asn Leu Ala Ser Thr
130                 135                 140                 145 gct atg tcc atc acc atc caa aga gac tgg gtt gtg gtt gtg gct gga      720
Ala Met Ser Ile Thr Ile Gln Arg Asp Trp Val Val Val Val Ala Gly
                150                 155                 160 gat gat cgg agc aaa ttg gca gat atg aat gca act gtc aga ata att      768
Asp Asp Arg Ser Lys Leu Ala Asp Met Asn Ala Thr Val Arg Ile Ile
            165                 170                 175 gac cag ttg acc aac att ctg gca ccg atg ctt gtg ggc cag atc atg      816
Asp Gln Leu Thr Asn Ile Leu Ala Pro Met Leu Val Gly Gln Ile Met
        180                 185                 190 gca ttt ggc tca cac ttc att ggc tgt ggt ttt atc tcg ggc tgg aac      864
Ala Phe Gly Ser His Phe Ile Gly Cys Gly Phe Ile Ser Gly Trp Asn
    195                 200                 205 ttg ttc tcc atg tgc ctg gag tat ttc ctg ctt tgg aaa gtt tat cag      912
Leu Phe Ser Met Cys Leu Glu Tyr Phe Leu Leu Trp Lys Val Tyr Gln
210                 215                 220                 225 aaa act cca gcg ctt gcc ttt aag gca gga cag aag gat agc gat gac      960
Lys Thr Pro Ala Leu Ala Phe Lys Ala Gly Gln Lys Asp Ser Asp Asp
                230                 235                 240 caa gag ctg aaa cac ctc aac ata caa aaa gaa att gga aac act gaa     1008
Gln Glu Leu Lys His Leu Asn Ile Gln Lys Glu Ile Gly Asn Thr Glu
            245                 250                 255 agc ccg gtc gaa gcc tcc caa ctg atg act gaa agc tcc gag ccc aag     1056
Ser Pro Val Glu Ala Ser Gln Leu Met Thr Glu Ser Ser Glu Pro Lys
        260                 265                 270 aag gac acc ggc tgc tgc tac caa atg gca gag ccc atc cgt acc ttt     1104
Lys Asp Thr Gly Cys Cys Tyr Gln Met Ala Glu Pro Ile Arg Thr Phe
    275                 280                 285 aaa gat ggc tgg gta gcc tac tac aat caa tcc atc ttc ttc gcc ggc     1152
Lys Asp Gly Trp Val Ala Tyr Tyr Asn Gln Ser Ile Phe Phe Ala Gly
290                 295                 300                 305 atg tct ctg gct ttc cta tac atg acc gtt ttg ggc ttc gac tgc atc     1200
Met Ser Leu Ala Phe Leu Tyr Met Thr Val Leu Gly Phe Asp Cys Ile
                310                 315                 320
```

```
acc aca ggc tat gca tac act cag ggc ctg aat ggc tct gtg ctc agt      1248
Thr Thr Gly Tyr Ala Tyr Thr Gln Gly Leu Asn Gly Ser Val Leu Ser
            325                 330                 335 ctc ctc atg gga gcc tca gct gta tct ggg atc tgt ggg aca gtg gcc      1296
Leu Leu Met Gly Ala Ser Ala Val Ser Gly Ile Cys Gly Thr Val Ala
            340                 345                 350 ttc acc tgg atc cga aag aag tgc ggc ctc atc agg acg ggc ttc att      1344
Phe Thr Trp Ile Arg Lys Lys Cys Gly Leu Ile Arg Thr Gly Phe Ile
            355                 360                 365 gct gga gtc acc cag ctg tcc tgc ctc acg ctg tgt gta gca tct gtc      1392
Ala Gly Val Thr Gln Leu Ser Cys Leu Thr Leu Cys Val Ala Ser Val
370                 375                 380                 385 ttc gcc cct ggt agc cct ttc gat ctc agc gtc tcg ccc ttc aaa gag      1440
Phe Ala Pro Gly Ser Pro Phe Asp Leu Ser Val Ser Pro Phe Lys Glu
                390                 395                 400 gtc tta aga cat ctg ttt gga gac agc ggc tcg ctg cgt gag agt cct      1488
Val Leu Arg His Leu Phe Gly Asp Ser Gly Ser Leu Arg Glu Ser Pro
                405                 410                 415 aca ttc att cct aca act gaa ccc ccg att cag gcc aac gtc acc gtt      1536
Thr Phe Ile Pro Thr Thr Glu Pro Pro Ile Gln Ala Asn Val Thr Val
                420                 425                 430 ttt gag gaa gcc ccc cca gta gag tcc tac atg tct gtt ggg ctt ctc      1584
Phe Glu Glu Ala Pro Pro Val Glu Ser Tyr Met Ser Val Gly Leu Leu
            435                 440                 445 ttt gcc ggt gtt att gct gct aga gtt ggt ctt tgg tcc ttc gac ttg      1632
Phe Ala Gly Val Ile Ala Ala Arg Val Gly Leu Trp Ser Phe Asp Leu
450                 455                 460                 465 acc gtg acc caa ctg atc caa gag aat gtg att gag tcc gag aga gga      1680
Thr Val Thr Gln Leu Ile Gln Glu Asn Val Ile Glu Ser Glu Arg Gly
                470                 475                 480 gtc atc aat ggc gtc cag aac tcc atg aat tat ctt ctc gat ctc ctg      1728
Val Ile Asn Gly Val Gln Asn Ser Met Asn Tyr Leu Leu Asp Leu Leu
                485                 490                 495 cac ttc atc atg gtc atc ctt gca cca aat cct gaa gcc ttt ggt ctt      1776
His Phe Ile Met Val Ile Leu Ala Pro Asn Pro Glu Ala Phe Gly Leu
                500                 505                 510 ctt gta atc atc tcc gtt tcc ttc gtg gct atg gga cat atg atg tat      1824
Leu Val Ile Ile Ser Val Ser Phe Val Ala Met Gly His Met Met Tyr
            515                 520                 525 ttc agg ttt gct tat aaa agc ctt gga agc cga ctc ttc ctg ttc tgt      1872
Phe Arg Phe Ala Tyr Lys Ser Leu Gly Ser Arg Leu Phe Leu Phe Cys
530                 535                 540                 545 tca ccc gag cag aag cca gat ccc aac att ccc tca ctt cca aac tct      1920
Ser Pro Glu Gln Lys Pro Asp Pro Asn Ile Pro Ser Leu Pro Asn Ser
                550                 555                 560 gta tag cttttaaag agaccgtagg ccatttctac aagagcgtgg cttgctgtgt       1976
Val * tctttcagaa ccttgccagg atcccatctg ttttactaac atgcatgctt ttgctgcttg   2036
cagtgctgtg cattgagtaa atatcctctg ccataggcta aaataacaaa gagaaggagc   2096
tcttcttagc atagcatact tcacttctca tatcatgttc aaggtgctgt aaaaatgcca   2156
tagaagcaac cgtaggagga aatatataca tggaaactac ggttctatca tgctttaatg   2216
acttttgtaa gagctccaaa gcaaaaatta gcatatttat tctactttta cgtattatat   2276 tgttttttt tttcaacttt atggtcgtag ttaaccttca gactggttat gacagttttg    2336
caatgtgctc tacttatgat agtgtagttt tgtaatgttt gtcccttctt ccaagccttg   2396
gttaaagtct ctttaatagc tattaagagt gcgctagtta tacattcagg taagcctata   2456
```

-continued

```
taatgcctat atatttatat acacgtgtag tcagtattct ttatctcagc ttcggtggtg    2516
ctacgttgtt tcaactcttt tggaaagcca tgcaggcggt ttatacatgt aaccaaagtg    2576
ggttttttt ggcatcacgt ggaagtgagg gaattgccgt ttttttatcg tgttaaacat     2636
tccatattat tattattacc ggtgtgatga tttcttggag atttaggcgc tgataggctc    2696
cccatcgcag caagagattt tagcgctagg tatttgtgct cctgtttgat tgaaagtga    2756
ttttcgcaca taattcttgt tttatttgc aaagattgtt acacatgcac tttacatgat    2816
taatatacgt tttccattac gaaacaagcg caacaagccc tcaggtatta cgatatttgc    2876
acaatacaca aaacctgtcg ccgaagttca cggccaggca ggaaatctga tattttaca    2936
tgcaaattta tttcaaaatg ggattttcaa agtacattaa cctcaaactt catgattttt    2996
accttcctat ataagacacc acacctcata cgctaatcta gattttctat aatacaaagt    3056
aaaggttaca gactgttcta ttagctgaga tgaaagccac aatcatagaa gtactactaa    3116
catccttta aaaccacagc tggctcgaca tagatatata gatatatata tatgaggtgt    3176
tttataatag ttgtgtaata ttgatgttgg acaccagcgg gaatccacca tatgcacaga    3236
acagagaagg gattattgag tccagtgtgt gaacggctgg tttgcagcgc agctggttcc    3296
aaacacaggt gccaagtcac acttgacttg ctaagttagc gttttcttta atgtgtgaga    3356
actacttcat gaggccccaa cgaacacact gtcagtcttt cattgtgtca gtctttctgt    3416
gaatgtgaag ccttatttac atctgtaaaa tattttttta tattcttatg ttgactagtt    3476
ttgtttcaat cgggtttatc ctcctttgta aggccacaga tttcccccctt ttagacaaga    3536
gaagtaaaca catttgcaat aaattgtact ttcgacaccc agttgaatgt aacagaagaa    3596
cctagattat tctttatata agcatattga ttctgttcat gtttggtggc atatttgcaa    3656
taattgtggt tcacactcca tcgcagtggg aggattatag aactttagtc ttgtattgta    3716
tctcacttcg actgaaataa acagatttgt atctaaaaaa aaaaaaaaaa aaaaaaa      3773
```

<210> SEQ ID NO 2
<211> LENGTH: 562
<212> TYPE: PRT
<213> ORGANISM: Danio rerio

<400> SEQUENCE: 2

```
Met Asp Ser Pro Ala Ser Lys Lys Pro Arg Cys Glu Arg Phe Arg Glu
  1               5                  10                  15

Phe Phe Lys Ser Ala Lys Phe Leu Ile Tyr Val Gly His Ala Leu Ser
             20                  25                  30

Thr Trp Gly Asp Arg Met Trp Asn Phe Ala Val Ala Val Phe Leu Val
         35                  40                  45

Glu Leu Tyr Gly Asn Ser Leu Leu Leu Thr Ala Val Tyr Gly Leu Val
     50                  55                  60

Val Ala Gly Ser Val Leu Leu Gly Ala Ile Ile Gly Asp Trp Val
 65                  70                  75                  80

Asp Lys Asn Pro Arg Leu Lys Val Ala Gln Thr Ser Leu Val Val Gln
                 85                  90                  95

Asn Ser Ala Val Ile Leu Cys Gly Ala Leu Leu Met Ala Val Phe Gln
            100                 105                 110

Phe Lys Gln Gln Leu Ser Ser Met Tyr Asp Gly Trp Leu Leu Thr Thr
        115                 120                 125

Cys Tyr Ile Met Val Ile Ser Ile Ala Asn Ile Ala Asn Leu Ala Ser
    130                 135                 140

Thr Ala Met Ser Ile Thr Ile Gln Arg Asp Trp Val Val Val Val Ala
```

-continued

```
            145                 150                 155                 160
Gly Asp Asp Arg Ser Lys Leu Ala Asp Met Asn Ala Thr Val Arg Ile
                165                 170                 175

Ile Asp Gln Leu Thr Asn Ile Leu Ala Pro Met Leu Val Gly Gln Ile
            180                 185                 190

Met Ala Phe Gly Ser His Phe Ile Gly Cys Gly Phe Ile Ser Gly Trp
            195                 200                 205

Asn Leu Phe Ser Met Cys Leu Glu Tyr Phe Leu Leu Trp Lys Val Tyr
            210                 215                 220

Gln Lys Thr Pro Ala Leu Ala Phe Lys Ala Gly Gln Lys Asp Ser Asp
225                 230                 235                 240

Asp Gln Glu Leu Lys His Leu Asn Ile Gln Lys Glu Ile Gly Asn Thr
                245                 250                 255

Glu Ser Pro Val Glu Ala Ser Gln Leu Met Thr Glu Ser Ser Glu Pro
            260                 265                 270

Lys Lys Asp Thr Gly Cys Cys Tyr Gln Met Ala Glu Pro Ile Arg Thr
                275                 280                 285

Phe Lys Asp Gly Trp Val Ala Tyr Tyr Asn Gln Ser Ile Phe Phe Ala
            290                 295                 300

Gly Met Ser Leu Ala Phe Leu Tyr Met Thr Val Leu Gly Phe Asp Cys
305                 310                 315                 320

Ile Thr Thr Gly Tyr Ala Tyr Thr Gln Gly Leu Asn Gly Ser Val Leu
                325                 330                 335

Ser Leu Leu Met Gly Ala Ser Ala Val Ser Gly Ile Cys Gly Thr Val
            340                 345                 350

Ala Phe Thr Trp Ile Arg Lys Lys Cys Gly Leu Ile Arg Thr Gly Phe
            355                 360                 365

Ile Ala Gly Val Thr Gln Leu Ser Cys Leu Thr Leu Cys Val Ala Ser
            370                 375                 380

Val Phe Ala Pro Gly Ser Pro Phe Asp Leu Ser Val Ser Pro Phe Lys
385                 390                 395                 400

Glu Val Leu Arg His Leu Phe Gly Asp Ser Gly Ser Leu Arg Glu Ser
                405                 410                 415

Pro Thr Phe Ile Pro Thr Thr Glu Pro Pro Ile Gln Ala Asn Val Thr
            420                 425                 430

Val Phe Glu Glu Ala Pro Pro Val Glu Ser Tyr Met Ser Val Gly Leu
            435                 440                 445

Leu Phe Ala Gly Val Ile Ala Ala Arg Val Gly Leu Trp Ser Phe Asp
            450                 455                 460

Leu Thr Val Thr Gln Leu Ile Gln Glu Asn Val Ile Glu Ser Glu Arg
465                 470                 475                 480

Gly Val Ile Asn Gly Val Gln Asn Ser Met Asn Tyr Leu Leu Asp Leu
                485                 490                 495

Leu His Phe Ile Met Val Ile Leu Ala Pro Asn Pro Glu Ala Phe Gly
            500                 505                 510

Leu Leu Val Ile Ile Ser Val Ser Phe Val Ala Met Gly His Met Met
            515                 520                 525

Tyr Phe Arg Phe Ala Tyr Lys Ser Leu Gly Ser Arg Leu Phe Leu Phe
            530                 535                 540

Cys Ser Pro Glu Gln Lys Pro Asp Pro Asn Ile Pro Ser Leu Pro Asn
545                 550                 555                 560

Ser Val
```

<210> SEQ ID NO 3
<211> LENGTH: 2130
<212> TYPE: DNA
<213> ORGANISM: Mus musculus
<220> FEATURE:
<221> NAME/KEY: CDS
<222> LOCATION: (298)...(2010)

<400> SEQUENCE: 3

```
agagcaggct gggggtctcc tgcggccggt ggatcctcca acccgctccc ataaggcttt      60
ggctttccaa cttcagctac agtgttagct aagtttggaa agaagacaaa aagaagaccc     120
cgtgacagct tgctgttgt tgtttgcctt agttgtcctt tggggtcttt cggcataagg     180
ctgttgtgct tatactggtg ctatcttcgg ttcctctcac tcctgtgaac aagctcccgg    240
gcaagagcag ctaaagctac cagcatcaga acaaacaagg ggagaacgcc tggtgtc atg   300
                                                              Met
                                                                1 acc aag gca aga gat caa acc cat cag gaa gga tgc tgt gga tcc tta     348
Thr Lys Ala Arg Asp Gln Thr His Gln Glu Gly Cys Cys Gly Ser Leu
        5                  10                  15 gca aac tac ctg acc tca gca aaa ttc ctc ctc tac ctt ggc cac tct     396
Ala Asn Tyr Leu Thr Ser Ala Lys Phe Leu Leu Tyr Leu Gly His Ser
     20                  25                  30 ctc tcc act tgg ggg gat cgg atg tgg cac ttt gca gtg tct gtg ttt     444
Leu Ser Thr Trp Gly Asp Arg Met Trp His Phe Ala Val Ser Val Phe
 35                  40                  45 ctg gtg gaa ctc tat gga aac agc ctt ctc ttg aca gct gtc tat gga     492
Leu Val Glu Leu Tyr Gly Asn Ser Leu Leu Leu Thr Ala Val Tyr Gly
 50                  55                  60                  65 ctg gtg gtg gca ggc tct gtt ctg gtc ctg gga gcc atc att ggt gac     540
Leu Val Val Ala Gly Ser Val Leu Val Leu Gly Ala Ile Ile Gly Asp
             70                  75                  80 tgg gtg gat aag aat gcc aga ctt aaa gtg gcc cag acg tca ctg gtg     588
Trp Val Asp Lys Asn Ala Arg Leu Lys Val Ala Gln Thr Ser Leu Val
         85                  90                  95 gtt cag aat gtg tcc gtc atc ctc tgc gga atc atc ctg atg atg gtt     636
Val Gln Asn Val Ser Val Ile Leu Cys Gly Ile Ile Leu Met Met Val
    100                 105                 110 ttc cta cac aag aat gag ctc ctg acc atg tac cat gga tgg gtc ctt     684
Phe Leu His Lys Asn Glu Leu Leu Thr Met Tyr His Gly Trp Val Leu
115                 120                 125 act gtc tgc tac atc ctg atc atc act att gca aac att gca aat ttg     732
Thr Val Cys Tyr Ile Leu Ile Ile Thr Ile Ala Asn Ile Ala Asn Leu
130                 135                 140                 145 gcc agt act gcc act gcg atc aca atc caa agg gac tgg att gtt gtt     780
Ala Ser Thr Ala Thr Ala Ile Thr Ile Gln Arg Asp Trp Ile Val Val
            150                 155                 160 gtg gca gga gaa aac agg agc aga tta gca gac atg aat gct acc att     828
Val Ala Gly Glu Asn Arg Ser Arg Leu Ala Asp Met Asn Ala Thr Ile
        165                 170                 175 aga agg att gac cag cta acc aac atc ctg gcc ccc atg gct gtc ggc     876
Arg Arg Ile Asp Gln Leu Thr Asn Ile Leu Ala Pro Met Ala Val Gly
    180                 185                 190 cag att atg aca ttt ggt tct cca gtc att ggc tgt ggt ttt att tcc     924
Gln Ile Met Thr Phe Gly Ser Pro Val Ile Gly Cys Gly Phe Ile Ser
195                 200                 205 ggt tgg aat ttg gtg tcc atg tgt gtg gag tac ttc ttg ctc tgg aag     972
Gly Trp Asn Leu Val Ser Met Cys Val Glu Tyr Phe Leu Leu Trp Lys
210                 215                 220                 225 gtt tac cag aag acc cct gct ctg gct gta aaa gct gct ctc aag gta    1020
Val Tyr Gln Lys Thr Pro Ala Leu Ala Val Lys Ala Ala Leu Lys Val
```

-continued

|     |     |     |     |     |
|-----|-----|-----|-----|-----|
|     | 230 | 235 | 240 |     | gag gag tca gaa ctg aag cag ctg acc tca cct aaa gat act gag cca   1068
Glu Glu Ser Glu Leu Lys Gln Leu Thr Ser Pro Lys Asp Thr Glu Pro
        245                 250                 255 aaa cct ttg gag gga act cat cta atg ggt gag aaa gac tcc aac atc   1116
Lys Pro Leu Glu Gly Thr His Leu Met Gly Glu Lys Asp Ser Asn Ile
                260                 265                 270 cgt gaa ctt gaa tgt gaa caa gag ccc acc tgt gcc tcc cag atg gca   1164
Arg Glu Leu Glu Cys Glu Gln Glu Pro Thr Cys Ala Ser Gln Met Ala
    275                 280                 285 gag ccc ttc cgc act ttc cga gat gga tgg gtc tcc tac tat aac cag   1212
Glu Pro Phe Arg Thr Phe Arg Asp Gly Trp Val Ser Tyr Tyr Asn Gln
290                 295                 300                 305 cca gtg ttt ctg gct ggc atg ggc ctg gct ttc ctc tat atg aca gtc   1260
Pro Val Phe Leu Ala Gly Met Gly Leu Ala Phe Leu Tyr Met Thr Val
                310                 315                 320 ctg ggc ttt gac tgt atc act aca ggg tac gcc tac act cag ggg ctg   1308
Leu Gly Phe Asp Cys Ile Thr Thr Gly Tyr Ala Tyr Thr Gln Gly Leu
                325                 330                 335 agt gga tcc atc ctt agt att ttg atg gga gca tca gca ata act gga   1356
Ser Gly Ser Ile Leu Ser Ile Leu Met Gly Ala Ser Ala Ile Thr Gly
        340                 345                 350 ata atg gga act gtg gcc ttc acc tgg cta cgt cga aaa tgt ggc ctt   1404
Ile Met Gly Thr Val Ala Phe Thr Trp Leu Arg Arg Lys Cys Gly Leu
355                 360                 365 gtt cgg act ggt cta ttc tca gga cta gcc cag ctt tcc tgt tta atc   1452
Val Arg Thr Gly Leu Phe Ser Gly Leu Ala Gln Leu Ser Cys Leu Ile
370                 375                 380                 385 ttg tgt gtg atc tcc gta ttc atg cct gga agc ccc ttg gac ctg tct   1500
Leu Cys Val Ile Ser Val Phe Met Pro Gly Ser Pro Leu Asp Leu Ser
                390                 395                 400 gtt tct cca ttt gaa gat atc cgt tct agg ttt gtg aat gtg gag cca   1548
Val Ser Pro Phe Glu Asp Ile Arg Ser Arg Phe Val Asn Val Glu Pro
        405                 410                 415 gtg tcc cca act acc aaa ata cct gag acc gtc ttt aca aca gaa atg   1596
Val Ser Pro Thr Thr Lys Ile Pro Glu Thr Val Phe Thr Thr Glu Met
                420                 425                 430 cat atg tcc aac atg tct aat gtc cat gag atg agt act aaa ccc atc   1644
His Met Ser Asn Met Ser Asn Val His Glu Met Ser Thr Lys Pro Ile
                435                 440                 445 ccc ata gtc tct gtc agc ctg ctg ttt gca gga gtc att gct gct aga   1692
Pro Ile Val Ser Val Ser Leu Leu Phe Ala Gly Val Ile Ala Ala Arg
450                 455                 460                 465 atc ggt ctt tgg tcc ttt gat ttg acg gtg aca cag ttg ctg caa gaa   1740
Ile Gly Leu Trp Ser Phe Asp Leu Thr Val Thr Gln Leu Leu Gln Glu
                470                 475                 480 aat gta att gaa tct gaa aga ggc att atc aat ggt gtg cag aac tcc   1788
Asn Val Ile Glu Ser Glu Arg Gly Ile Ile Asn Gly Val Gln Asn Ser
            485                 490                 495 atg aac tac ctt ctt gac ctt ctg cat ttc atc atg gtc atc ttg gcc   1836
Met Asn Tyr Leu Leu Asp Leu Leu His Phe Ile Met Val Ile Leu Ala
                500                 505                 510 cca aat cct gaa gct ttt ggc ttg ctg gta ttg att tca gtc tcc ttt   1884
Pro Asn Pro Glu Ala Phe Gly Leu Leu Val Leu Ile Ser Val Ser Phe
            515                 520                 525 gtg gca atg gga cat ctt atg tat ttc cga ttt gcc cag aag act ctg   1932
Val Ala Met Gly His Leu Met Tyr Phe Arg Phe Ala Gln Lys Thr Leu
530                 535                 540                 545 ggc aac cag att ttt gtt tgt ggt cct gat gaa aaa gaa gtt aca gat   1980
Gly Asn Gln Ile Phe Val Cys Gly Pro Asp Glu Lys Glu Val Thr Asp

```
                550             555             560
gaa aat caa ccg aat aca tct gtt gta taa aaatagttta gctgtggccc    2030
Glu Asn Gln Pro Asn Thr Ser Val Val  *
            565             570 ctgttactag attgtggaga gcatgtgtgc ttattttgta ctgcagaatc ccaataaatg    2090
cctgcatttc tctccaaaaa aaaaaaaaaa aaaaaaaaa    2130

<210> SEQ ID NO 4
<211> LENGTH: 570
<212> TYPE: PRT
<213> ORGANISM: Mus musculus

<400> SEQUENCE: 4

Met Thr Lys Ala Arg Asp Gln Thr His Gln Glu Gly Cys Cys Gly Ser
 1               5                  10                  15

Leu Ala Asn Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
           100                 105                 110

Val Phe Leu His Lys Asn Glu Leu Leu Thr Met Tyr His Gly Trp Val
        115                 120                 125

Leu Thr Val Cys Tyr Ile Leu Ile Ile Thr Ile Ala Asn Ile Ala Asn
    130                 135                 140

Leu Ala Ser Thr Ala Thr Ala Ile Thr Ile Gln Arg Asp Trp Ile Val
145                 150                 155                 160

Val Val Ala Gly Glu Asn Arg Ser Arg Leu Ala Asp Met Asn Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Phe Leu Leu Trp
    210                 215                 220

Lys Val Tyr Gln Lys Thr Pro Ala Leu Ala Val Lys Ala Ala Leu Lys
225                 230                 235                 240

Val Glu Glu Ser Glu Leu Lys Gln Leu Thr Ser Pro Lys Asp Thr Glu
                245                 250                 255

Pro Lys Pro Leu Glu Gly Thr His Leu Met Gly Glu Lys Asp Ser Asn
            260                 265                 270

Ile Arg Glu Leu Glu Cys Glu Gln Glu Pro Thr Cys Ala Ser Gln Met
        275                 280                 285

Ala Glu Pro Phe Arg Thr Phe Arg Asp Gly Trp Val Ser Tyr Tyr Asn
    290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335
```

```
Leu Ser Gly Ser Ile Leu Ser Ile Leu Met Gly Ala Ser Ala Ile Thr
                340                 345                 350

Gly Ile Met Gly Thr Val Ala Phe Thr Trp Leu Arg Arg Lys Cys Gly
            355                 360                 365

Leu Val Arg Thr Gly Leu Phe Ser Gly Leu Ala Gln Leu Ser Cys Leu
    370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Val Asn Val Glu
                405                 410                 415

Pro Val Ser Pro Thr Thr Lys Ile Pro Glu Thr Val Phe Thr Thr Glu
            420                 425                 430

Met His Met Ser Asn Met Ser Asn Val His Glu Met Ser Thr Lys Pro
    435                 440                 445

Ile Pro Ile Val Ser Val Ser Leu Leu Phe Ala Gly Val Ile Ala Ala
450                 455                 460

Arg Ile Gly Leu Trp Ser Phe Asp Leu Thr Val Thr Gln Leu Leu Gln
465                 470                 475                 480

Glu Asn Val Ile Glu Ser Arg Gly Ile Ile Asn Gly Val Gln Asn
                485                 490                 495

Ser Met Asn Tyr Leu Leu Asp Leu Leu His Phe Ile Met Val Ile Leu
            500                 505                 510

Ala Pro Asn Pro Glu Ala Phe Gly Leu Leu Val Leu Ile Ser Val Ser
    515                 520                 525

Phe Val Ala Met Gly His Leu Met Tyr Phe Arg Phe Ala Gln Lys Thr
530                 535                 540

Leu Gly Asn Gln Ile Phe Val Cys Gly Pro Asp Glu Lys Glu Val Thr
545                 550                 555                 560

Asp Glu Asn Gln Pro Asn Thr Ser Val Val
                565                 570

<210> SEQ ID NO 5
<211> LENGTH: 2222
<212> TYPE: DNA
<213> ORGANISM: Homo sapiens
<220> FEATURE:
<221> NAME/KEY: CDS
<222> LOCATION: (305)...(2020)

<400> SEQUENCE: 5
agctggctca gggcgtccgc taggctcgga cgacctgctg agcctcccaa accgcttcca    60
taaggctttg ctttccaact tcagctacag tgttagctaa gtttggaaag aaggaaaaaa   120
gaaaatccct gggccccttt tcttttgttc tttgccaaag tcgtcgttgt agtcttttg    180 cccaaggctg ttgtgttttt agaggtgcta tctccagttc cttgcactcc tgttaacaag   240
cacctcagcg agagcagcag cagcgatagc agccgcagaa gagccagcgg ggtcgcctag   300 tgtc atg acc agg gcg gga gat cac aac cgc cag aga gga tgc tgt gga    349
     Met Thr Arg Ala Gly Asp His Asn Arg Gln Arg Gly Cys Cys Gly
     1               5                   10                  15 tcc ttg gcc gac tac ctg acc tct gca aaa ttc ctt ctc tac ctt ggt    397
Ser Leu Ala Asp Tyr Leu Thr Ser Ala Lys Phe Leu Leu Tyr Leu Gly
             20                  25                  30 cat tct ctc tct act tgg gga gat cgg atg tgg cac ttt gcg gtg tct    445
His Ser Leu Ser Thr Trp Gly Asp Arg Met Trp His Phe Ala Val Ser
         35                  40                  45 gtg ttt ctg gta gag ctc tat gga aac agc ctc ctt ttg aca gca gtc    493
```

```
              Val Phe Leu Val Glu Leu Tyr Gly Asn Ser Leu Leu Leu Thr Ala Val
                          50                  55                  60 tac ggg ctg gtg gtg gca ggg tct gtt ctg gtc ctg gga gcc atc atc          541
Tyr Gly Leu Val Val Ala Gly Ser Val Leu Val Leu Gly Ala Ile Ile
             65                  70                  75 ggt gac tgg gtg gac aag aat gct aga ctt aaa gtg gcc cag acc tcg          589
Gly Asp Trp Val Asp Lys Asn Ala Arg Leu Lys Val Ala Gln Thr Ser
 80                  85                  90                  95 ctg gtg gta cag aat gtt tca gtc atc ctg tgt gga atc atc ctg atg          637
Leu Val Val Gln Asn Val Ser Val Ile Leu Cys Gly Ile Ile Leu Met
                    100                 105                 110 atg gtt ttc tta cat aaa cat gag ctt ctg acc atg tac cat gga tgg          685
Met Val Phe Leu His Lys His Glu Leu Leu Thr Met Tyr His Gly Trp
                115                 120                 125 gtt ctc act tcc tgc tat atc ctg atc atc act att gca aat att gca          733
Val Leu Thr Ser Cys Tyr Ile Leu Ile Ile Thr Ile Ala Asn Ile Ala
            130                 135                 140 aat ttg gcc agt act gct act gca atc aca atc caa agg gat tgg att          781
Asn Leu Ala Ser Thr Ala Thr Ala Ile Thr Ile Gln Arg Asp Trp Ile
145                 150                 155 gtt gtt gtt gca gga gaa gac aga agc aaa cta gca aat atg aat gcc          829
Val Val Val Ala Gly Glu Asp Arg Ser Lys Leu Ala Asn Met Asn Ala
160                 165                 170                 175 aca ata cga agg att gac cag tta acc aac atc tta gcc ccc atg gct          877
Thr Ile Arg Arg Ile Asp Gln Leu Thr Asn Ile Leu Ala Pro Met Ala
                180                 185                 190 gtt ggc cag att atg aca ttt ggc tcc cca gtc atc ggc tgt ggc ttt          925
Val Gly Gln Ile Met Thr Phe Gly Ser Pro Val Ile Gly Cys Gly Phe
            195                 200                 205 att tcg gga tgg aac ttg gta tcc atg tgc gtg gag tac gtc ctg ctc          973
Ile Ser Gly Trp Asn Leu Val Ser Met Cys Val Glu Tyr Val Leu Leu
        210                 215                 220 tgg aag gtt tac cag aaa acc cca gct cta gct gtg aaa gct ggt ctt          1021
Trp Lys Val Tyr Gln Lys Thr Pro Ala Leu Ala Val Lys Ala Gly Leu
    225                 230                 235 aaa gaa gag gaa act gaa ttg aaa cag ctg aat tta cac aaa gat act          1069
Lys Glu Glu Glu Thr Glu Leu Lys Gln Leu Asn Leu His Lys Asp Thr
240                 245                 250                 255 gag cca aaa ccc ctg gag gga act cat cta atg ggt gtg aaa gac tct          1117
Glu Pro Lys Pro Leu Glu Gly Thr His Leu Met Gly Val Lys Asp Ser
                260                 265                 270 aac atc cat gag ctt gaa cat gag caa gag cct act tgt gcc tcc cag          1165
Asn Ile His Glu Leu Glu His Glu Gln Glu Pro Thr Cys Ala Ser Gln
            275                 280                 285 atg gct gag ccc ttc cgt acc ttc cga gat gga tgg gtc tcc tac tac          1213
Met Ala Glu Pro Phe Arg Thr Phe Arg Asp Gly Trp Val Ser Tyr Tyr
        290                 295                 300 aac cag cct gtg ttt ctg gct ggc atg ggt ctt gct ttc ctt tat atg          1261
Asn Gln Pro Val Phe Leu Ala Gly Met Gly Leu Ala Phe Leu Tyr Met
    305                 310                 315 act gtc ctg ggc ttt gac tgc atc acc aca ggg tac gcc tac act cag          1309
Thr Val Leu Gly Phe Asp Cys Ile Thr Thr Gly Tyr Ala Tyr Thr Gln
320                 325                 330                 335 gga ctg agt ggt tcc atc ctc agt att ttg atg gga gca tca gct ata          1357
Gly Leu Ser Gly Ser Ile Leu Ser Ile Leu Met Gly Ala Ser Ala Ile
                340                 345                 350 act gga ata atg gga act gta gct ttt act tgg cta cgt cga aaa tgt          1405
Thr Gly Ile Met Gly Thr Val Ala Phe Thr Trp Leu Arg Arg Lys Cys
            355                 360                 365 ggt ttg gtt cgg aca ggt ctg atc tca gga ttg gca cag ctt tcc tgt          1453
```

```
Gly Leu Val Arg Thr Gly Leu Ile Ser Gly Leu Ala Gln Leu Ser Cys
        370                 375                 380 ttg atc ttg tgt gtg atc tct gta ttc atg cct gga agc ccc ctg gac    1501
Leu Ile Leu Cys Val Ile Ser Val Phe Met Pro Gly Ser Pro Leu Asp
385                 390                 395 ttg tcc gtt tct cct ttt gaa gat atc cga tca agg ttc att caa gga    1549
Leu Ser Val Ser Pro Phe Glu Asp Ile Arg Ser Arg Phe Ile Gln Gly
400                 405                 410                 415 gag tca att aca cct acc aag ata cct gaa att aca act gaa ata tac    1597
Glu Ser Ile Thr Pro Thr Lys Ile Pro Glu Ile Thr Thr Glu Ile Tyr
            420                 425                 430 atg tct aat ggg tct aat tct gct aat att gtc ccg gag aca agt cct    1645
Met Ser Asn Gly Ser Asn Ser Ala Asn Ile Val Pro Glu Thr Ser Pro
            435                 440                 445 gaa tct gtg ccc ata atc tct gtc agt ctg ctg ttt gca ggc gtc att    1693
Glu Ser Val Pro Ile Ile Ser Val Ser Leu Leu Phe Ala Gly Val Ile
            450                 455                 460 gct gct aga atc ggt ctt tgg tcc ttt gat tta act gtg aca cag ttg    1741
Ala Ala Arg Ile Gly Leu Trp Ser Phe Asp Leu Thr Val Thr Gln Leu
465                 470                 475 ctg caa gaa aat gta att gaa tct gaa aga ggc att ata aat ggt gta    1789
Leu Gln Glu Asn Val Ile Glu Ser Glu Arg Gly Ile Ile Asn Gly Val
480                 485                 490                 495 cag aac tcc atg aac tat ctt ctt gat ctt ctg cat ttc atc atg gtc    1837
Gln Asn Ser Met Asn Tyr Leu Leu Asp Leu Leu His Phe Ile Met Val
            500                 505                 510 atc ctg gct cca aat cct gaa gct ttt ggc ttg ctc gta ttg att tca    1885
Ile Leu Ala Pro Asn Pro Glu Ala Phe Gly Leu Leu Val Leu Ile Ser
            515                 520                 525 gtc tcc ttt gtg gca atg ggc cac att atg tat ttc cga ttt gcc caa    1933
Val Ser Phe Val Ala Met Gly His Ile Met Tyr Phe Arg Phe Ala Gln
            530                 535                 540 aat act ctg gga aac aag ctc ttt gct tgc ggt cct gat gca aaa gaa    1981
Asn Thr Leu Gly Asn Lys Leu Phe Ala Cys Gly Pro Asp Ala Lys Glu
545                 550                 555 gtt agg aag gaa aat caa gca aat aca tct gtt gtt tga gacagtttaa    2030
Val Arg Lys Glu Asn Gln Ala Asn Thr Ser Val Val *
560                 565                 570 ctgttgctat cctgttacta gattatatag agcacatgtg cttatttgt actgcagaat    2090 tccaataaat ggctgggtgt tttgctctgt ttttaccaca gctgtgcctt gagaactaaa    2150
agctgtttag gaaacctaag tcagcagaaa ttaactgatt aatttcccctt atgttgaggc    2210 atggaaaaaa aa                                                         2222

<210> SEQ ID NO 6
<211> LENGTH: 571
<212> TYPE: PRT
<213> ORGANISM: Homo sapiens

<400> SEQUENCE: 6

Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Ala Ile Ile Gly
```

```
                65                  70                  75                  80
Asp Trp Val Asp Lys Asn Ala Arg Leu Lys Val Ala Gln Thr Ser Leu
                    85                  90                  95
Val Val Gln Asn Val Ser Val Ile Leu Cys Gly Ile Ile Leu Met Met
                    100                 105                 110
Val Phe Leu His Lys His Glu Leu Leu Thr Met Tyr His Gly Trp Val
                    115                 120                 125
Leu Thr Ser Cys Tyr Ile Leu Ile Ile Thr Ile Ala Asn Ile Ala Asn
                    130                 135                 140
Leu Ala Ser Thr Ala Thr Ala Ile Thr Ile Gln Arg Asp Trp Ile Val
145                 150                 155                 160
Val Val Ala Gly Glu Asp Arg Ser Lys Leu Ala Asn Met Asn Ala Thr
                    165                 170                 175
Ile Arg Arg Ile Asp Gln Leu Thr Asn Ile Leu Ala Pro Met Ala Val
                    180                 185                 190
Gly Gln Ile Met Thr Phe Gly Ser Pro Val Ile Gly Cys Gly Phe Ile
                    195                 200                 205
Ser Gly Trp Asn Leu Val Ser Met Cys Val Glu Tyr Val Leu Leu Trp
                    210                 215                 220
Lys Val Tyr Gln Lys Thr Pro Ala Leu Ala Val Lys Ala Gly Leu Lys
225                 230                 235                 240
Glu Glu Glu Thr Glu Leu Lys Gln Leu Asn Leu His Lys Asp Thr Glu
                    245                 250                 255
Pro Lys Pro Leu Glu Gly Thr His Leu Met Gly Val Lys Asp Ser Asn
                    260                 265                 270
Ile His Glu Leu Glu His Glu Gln Glu Pro Thr Cys Ala Ser Gln Met
                    275                 280                 285
Ala Glu Pro Phe Arg Thr Phe Arg Asp Gly Trp Val Ser Tyr Tyr Asn
                    290                 295                 300
Gln Pro Val Phe Leu Ala Gly Met Gly Leu Ala Phe Leu Tyr Met Thr
305                 310                 315                 320
Val Leu Gly Phe Asp Cys Ile Thr Thr Gly Tyr Ala Tyr Thr Gln Gly
                    325                 330                 335
Leu Ser Gly Ser Ile Leu Ser Ile Leu Met Gly Ala Ser Ala Ile Thr
                    340                 345                 350
Gly Ile Met Gly Thr Val Ala Phe Thr Trp Leu Arg Arg Lys Cys Gly
                    355                 360                 365
Leu Val Arg Thr Gly Leu Ile Ser Gly Leu Ala Gln Leu Ser Cys Leu
                    370                 375                 380
Ile Leu Cys Val Ile Ser Val Phe Met Pro Gly Ser Pro Leu Asp Leu
385                 390                 395                 400
Ser Val Ser Pro Phe Glu Asp Ile Arg Ser Arg Phe Ile Gln Gly Glu
                    405                 410                 415
Ser Ile Thr Pro Thr Lys Ile Pro Glu Ile Thr Thr Glu Ile Tyr Met
                    420                 425                 430
Ser Asn Gly Ser Asn Ser Ala Asn Ile Val Pro Glu Thr Ser Pro Glu
                    435                 440                 445
Ser Val Pro Ile Ile Ser Val Ser Leu Leu Phe Ala Gly Val Ile Ala
                    450                 455                 460
Ala Arg Ile Gly Leu Trp Ser Phe Asp Leu Thr Val Thr Gln Leu Leu
465                 470                 475                 480
Gln Glu Asn Val Ile Glu Ser Glu Arg Gly Ile Asn Gly Val Gln
                    485                 490                 495
```

```
Asn Ser Met Asn Tyr Leu Leu Asp Leu Leu His Phe Ile Met Val Ile
            500                 505                 510

Leu Ala Pro Asn Pro Glu Ala Phe Gly Leu Leu Val Leu Ile Ser Val
        515                 520                 525

Ser Phe Val Ala Met Gly His Ile Met Tyr Phe Arg Phe Ala Gln Asn
    530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
                565                 570

<210> SEQ ID NO 7
<211> LENGTH: 7496
<212> TYPE: DNA
<213> ORGANISM: Homo sapiens

<400> SEQUENCE: 7
```

| | | | | | |
|---|---|---|---|---|---|
| agctggctca | gggcgtccgc | taggctcgga | cgacctgctg | agcctcccaa | accgcttcca | 60 |
| taaggctttg | ctttccaact | tcagctacag | tgttagctaa | gtttggaaag | aaggaaaaaa | 120 |
| gaaaatccct | gggccccttt | tcttttgttc | tttgccaaag | tcgtcgttgt | agtctttttg | 180 |
| cccaaggctg | ttgtgttttt | agaggtgcta | tctccagttc | cttgcactcc | tgttaacaag | 240 |
| cacctcagcg | agagcagcag | cagcgatagc | agccgcagaa | gagccagcgg | ggtcgcctag | 300 |
| tgtcatgacc | agggcgggag | atcacaaccg | ccagagagga | tgctgtggtg | agtgtcgttg | 360 |
| accgaaagca | tatggtggaa | acccaggtgg | ggctttggag | acaagcaact | ctacccgagt | 420 |
| tctggaggaa | tgtggctctg | ctgtgaacca | tagctttgta | aaaagatcct | ttgactcata | 480 |
| tttggtggac | gttaaggaag | aaaggaaatt | cagggtgtgg | gaaagggggt | ttgcacacag | 540 |
| gcacggatgg | agtagattgg | gcagtttgga | ttgccttgtg | taaaaaagaa | acaaaacaaa | 600 |
| ccaaccaacc | cacggggaa | aaacaaacc | aaacaaacca | accaacccaa | aaagaatgc | 660 |
| tgaaacaaga | gtttcttctc | tgtatgtgaa | atgtgaagtt | gggcagttat | tgactaggtc | 720 |
| aataactgaa | tttagtgaat | ggtattaagt | gaacgaaata | catcggttca | taggtaactt | 780 |
| gataaaatgt | acgtggtttg | tcctgcaaag | tagttttttaa | taatcatgtt | ctaatgagat | 840 |
| caaatggata | agcattctgc | cctcagctca | ttaagtgact | accatcgctt | tttctcaccc | 900 |
| cgcctgtgtc | tttgcaggat | ccttggccga | ctacctgacc | tctgcaaaat | tccttctcta | 960 |
| ccttggtcat | tctctctcta | cttgggtaag | tgagaatgca | tagtcttaca | acacagttgc | 1020 |
| gcaatttttt | atttcctttc | gttctagcca | gttgtattaa | gccaacttcc | agttttgtca | 1080 |
| agcagttaaa | gaaataaagg | gggaagagta | attactgact | ttgaaagtct | cataatgtag | 1140 |
| ccaggccgtg | cccttttgat | aaggaagcaa | cttcctgagt | acaatagact | agaaacgaaa | 1200 |
| aatattccat | caaacatttt | tctcttttca | tttaagggag | atcggatgtg | gcactttgcg | 1260 |
| gtgtctgtgt | ttctggtaga | gctctatgga | aacagcctcc | ttttgacagc | agtctacggg | 1320 |
| ctggtggtgg | cagggtctgt | tctggtcctg | ggagccatca | tcggtgactg | ggtggacaag | 1380 |
| aatgctagac | ttaaaggtga | gtgttgttat | ataattaagc | cctttattc | atgggaccaa | 1440 |
| tgcctgagct | acctctgtag | caaaggaaac | aacaaactag | gagagaaaca | accagggaat | 1500 |
| gtctgcatgc | cacacttgag | ggaggagggc | ttagatggca | ccacctctgg | atggagggtc | 1560 |
| ccatggctcc | cacacaaagt | tgggatgcct | ggacattgac | ctaatagatt | tttttgtatc | 1620 |
| tttggctgtt | cataaatttc | atatgttaat | gattaacctt | gtagcacttc | tctgagaacc | 1680 |
| atgttaaaca | ttaaaagttt | gcttaactca | ggcttcctaa | ctgtatcttg | tactggagtc | 1740 |

```
cctttagtgt gatgttcctg agacagcttt aacatctgtt ctttggttac tatgtttcat    1800
gtaagagtat gtataaggga attgaaaact aagaatagct tcaaggcaga atagttgagc    1860
ctggatcaca aagagctgaa ttataaattt tgtagggaaa aagaagaaat aataatatct    1920
tgatatttat tctaagcatt agtactgaaa tcatgtcatt ttatacagga aaagaaagta    1980
attgatcaat taaattttc agtatataag ggaaatatgg atgatcattc agggtaaatt     2040
ttcttgaatt gctcaattga taatggccaa gaacctgacc atgcctgact tagggggatg    2100
taggttcctg ccttaatcat ctgctactga gggcagagaa aaggctacca ggtgtcttta    2160
tctgtcctta ctccagtgct ttatctatat gggcgcctca taagagagtt gccatctgtg    2220
atgaaagggg agcttagaat tcgtagcaa tggcaaatag cgttagtatg caaagaaata     2280
ccctgctgct ttattctggg caaattttg tgtgtctttt ctatttaggt aagccatatt     2340
atcagattca gcctgccatg taggaggttg taggtttgat aacttcctct ttaacctcat    2400
acatgttatt gttttacctt aagcaacaaa gagctgaaat gtggatcatg tctatatcat    2460
actacagctc catttatgtt aaactttcaa gaagataaac taaatgaaaa ggtagtcatt    2520
atgatagact tcagtgagca gagaagcttg tggtacttca tcatttggtt tgcatattta    2580
ctggtctggt gtgatcctct gggttgtatt gagagtagtt gaggcaggac tgacttcaga    2640
aaggttttct ttttatctgg taataattag gtctgggtat taatgtatta tagtagagca    2700
attatgtgtg gataagagca gtctcagtga gccatttga tgtaatgtac actttctctc     2760
ttcctctgca cagtggccca gacctcgctg gtggtacaga atgtttcagt catcctgtgt    2820
ggaatcatcc tgatgatggt tttcttacat aaacatgagc ttctgaccat gtaccatgga    2880
tgggttctcg taagttctca atgagattct tgatggcaga aaattgaata tctggtagtg    2940
gtaaaggatg aaaatgcttt gaagctattt ttttttggg ggagggatgg ggtgtggtat     3000
aacccatgca tctggtgtca tattgaatct tcttgtgtat atgtggattg atattataga    3060
gttgcaaagc caggtaggac tttagaaatc tttgagccta ttcccttcat tttattgaaa    3120
aaattaagac aaagtgaacg ttagttgatt gcccattgtc atgcaactag aaggtgtcag    3180
aactctgact taaatacagg tgttttcaat tccccttcaa cattctttc aaaggcaata     3240
tttgtgggag aaatgttcaa aaccaccact gtgttaacat tttataactg tattcacctg    3300
actattataa ttttgtatt atgtgtacta cagatgatct agatgataca ggttaggaca     3360
ttatgcccat tgactactgg tattcattca gtttcatatc tataacgtaa atgatttct     3420
tataaatgaa attaaaatac tttttttatc attccaccaa agactatttt aaactgcctt    3480
gtttagtgac atatgtacag tgtggtaaac tgacattata actcattttt ttcttgtcat    3540
tctttagact tcctgctata tcctgatcat cactattgca aatattgcaa atttggccag    3600
tactgctact gcaatcacaa tccaaaggga ttggattgtt gttgttgcag gagaagacag    3660
aagcaaaacta gcaagtaatt tggctttctc ttttaatgaa atgagcatgt taggattcac   3720
tttaaatcgg tggtgataaa tgaggctgta agcttgtatt tttgttctgg gtattttta    3780
agaatgataa attgaaagca tacttttttc ttaccttatt gtcagtttta gtgctgattt    3840
atctcactgt tacgaagtta acttatagga tagctaactt ctctttatcc tacgggggaa   3900
accaacattt taggaatcta tactcttggt ttacagcttt gtattgtgta aatgggcagt   3960
ctctctttga tggggtttgca cacttacctg cctctttcac cggcctctct agatatgaat  4020
gccacaatac gaaggattga ccagttaacc aacatcttag cccccatggc tgttggccag   4080
attatgacat ttggctcccc agtcatcggc tgtggcttta tttcgggatg gaacttggta   4140
```

```
tccatgtgcg tggagtacgt cctgctctgg aaggtttacc agaaaacccc agctctagct    4200
gtgaaagctg gtcttaaaga agaggaaact gaattgaaac agctgaattt acacaaaggt    4260
aaactgaaca caatgatctc tccttttgtt ctcatgttca gaccttaaat gttggtgaag    4320
atcaaaacta ttttgaattt gtatcaggtt ttattaccag tgggggccag atgaggttaa    4380
atatatcgct ttggtagacg aggcaagagc aggcttttga ggatctaggg aaaaactccg    4440
ggttgaatct ggtgggtta gaatgggtcc cctagccctc ttccttgatg tgagcagtag     4500
ttatagaggt tcaattttac ttgagagata gctgggcaaa gctaagtcat aggactggga    4560
aaaaatgtgg ggaaaaaaag agaatgagag aatcccttgg actctgtgag gagggagtta    4620
tgtagtcatt tgtaggacag tggaagggag tgaggacaca aagatgggta tttcactgga    4680
gaagaggacg ctgggcttct gggtaaacag aatctttat ccactctgca gggacccaga     4740
aaataatatg ctggttgttt tttgtttttt tgagacagag tctcgctctg ttgcccaggc    4800
tgaagtgcag tggcgcgatc ttggctcact gcaagctctg cctcctgggt tcacgccatt    4860
ctcctgcctc agcctcccaa gtagctggga ttgcaggcat ccaccaccac acccggctaa    4920
ttttttgtat tttagtaga gacggggttt caccatgtta gccaggatgg tcttgatctc      4980
ctgacctcgt gatctgcccg cctcggcctc ccaaagtgct gggattacag gtgtgagcca    5040
ccgtgcctgg ccaatacgct gtgtttttt agacaatttt aatattttat ctggtgagtt      5100
ttcctgctgt ttactttggt gggagtataa tttctaagag caagagagag agagaaaaaa    5160
aagagggata gatcaatagt attttgttta tttaataaaa atgacacttg atgattattc    5220
cttggctgga attcttagat tattagtaaa agaaaataca tattacaatg tctaaccaag    5280
ggtacccatt gggaagggga atagaaggaa aaaaagtact actaataatt ggcttttatt    5340
tctacatgtc ctccccaaca aaataatggt atcttttctt aacagatact gagccaaaac    5400
ccctggaggg aactcatcta atgggtgtga aagactctaa catccatgag cttgaacatg    5460
agcaagagcc tacttgtgcc tcccagatgg ctgagccctt ccgtaccttc cgagatggat    5520
gggtctccta ctacaaccag cctgtgtttc tggctggcat gggtcttgct ttcctttata    5580
tgactgtcct gggctttgac tgcatcacca cagggtacgc ctacactcag ggactgagtg    5640
gttccatcct cagtattttg atgggagcat cagctataac tggaataatg ggaactgtag    5700
cttttacttg gctacgtcga aaatgtggtt tggttcggac aggtctgatc tcaggattgg    5760
cacagctttc ctgtttgatc ttgtgtgtga tctctgtatt catgcctgga agccccctgg    5820
acttgtccgt ttctcctttt gaagatatcc gatcaaggtt cattcaagga gagtcaatta    5880
cacctaccaa gatacctgaa attacaactg aaatatacat gtctaatggg tctaattctg    5940
ctaatattgt cccggagaca agtcctgaat ctgtgcccat aatctctgtc agtctgctgt    6000
ttgcaggcgt cattgctgct agaatcggta agaaatctct ttttatatat taatgaacta    6060
aagtgtcttt ttgtaatgta ggttcagaga atccattaat aaatgatctg aaatgttccc    6120
taaatgttaa tttaagcaaa atccactctt acgaaatttt tatttacat atttatactt     6180 tatatttatt gtgtttttta ttttatagtt tgaaacctg tatttgttta ctttattata      6240
tacatatact taaaacatgg ttcaggcttg aaaataattt tttctaaatg aatatcttaa    6300
atattacggg ggcaaaggtc ttctctagcc atatgtattt attatatagt ttgccacaca    6360
aatggatttt atagccctgg aaggaaacat aaagacttct tacaaagcaa aatttaagta    6420
ataattaata gagtactgat gaattatctc tgaattcagt cttgaaatga aactgttttt    6480
atcttgtgat acaaaacagt tcattagttt attgaagata ttaatttcca ggcaagacag    6540
```

```
cttattgtt tgggctttag aactctagca gtaatataac aatggtttaa agtttcctta    6600
cactttaacc ataaccattt attaggtcat ttgaaactta aaaatactaa gtacttatac   6660
tataatagga tttattatgt ctctgatttc aaagttttgt ttttgtagta tgaataatca   6720
cagaaaaaca gaactaagaa gtttgtagat tagacttctt tttgtctgat gactgtaaaa   6780
atcatttatt gaggccacta ataacccaat atttatttat gaaaataat tcttaaggca    6840 aggctatggt atatttaagg tgacttaaag acagtcaggc taaaatgtat attttgcata   6900
tgtcaacaga ttttatctg tgatttgaaa tgtatgcctg taaactaaaa tctaatcttt    6960 aaaaaatat tttattatag gtctttggtc ctttgattta actgtgacac agttgctgca    7020
agaaaatgta attgaatctg aaagaggcat tataaatggt gtacagaact ccatgaacta   7080
tcttcttgat cttctgcatt tcatcatggt catcctggct ccaaatcctg aagcttttgg   7140
cttgctcgta ttgatttcag tctcctttgt ggcaatgggc cacattatgt atttccgatt   7200
tgcccaaaat actctgggaa acaagctctt tgcttgcgt cctgatgcaa aagaagttag    7260
gaaggaaaat caagcaaata catctgttgt ttgagacagt ttaactgttg ctatcctgtt   7320
actagattat atagagcaca tgtgcttatt ttgtactgca gaattccaat aaatggctgg   7380
gtgttttgct ctgtttttac cacagctgtg ccttgagaac taaaagctgt ttaggaaacc   7440
taagtcagca gaaattaact gattaatttc ccttatgttg aggcatggaa aaaaaa       7496
```

<210> SEQ ID NO 8
<211> LENGTH: 19
<212> TYPE: DNA
<213> ORGANISM: Danio rerio

<400> SEQUENCE: 8 aaa gaa gtg cgg cct cat c                                           19

<210> SEQ ID NO 9
<211> LENGTH: 19
<212> TYPE: DNA
<213> ORGANISM: Danio rerio
<220> FEATURE:
<221> NAME/KEY: mutation
<222> LOCATION: 10
<223> OTHER INFORMATION: wehth238 allele

<400> SEQUENCE: 9 aaa gaa gtg agg cct cat c                                           19

<210> SEQ ID NO 10
<211> LENGTH: 19
<212> TYPE: DNA
<213> ORGANISM: Danio rerio

<400> SEQUENCE: 10 gag caa att ggc agg taa g                                           19

<210> SEQ ID NO 11
<211> LENGTH: 19
<212> TYPE: DNA
<213> ORGANISM: Danio rerio
<220> FEATURE:
<221> NAME/KEY: mutation
<222> LOCATION: 10
<223> OTHER INFORMATION: wehtp85c allele

<400> SEQUENCE: 11 gag caa att tgc agg taa g                                           19

```
<210> SEQ ID NO 12
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 12 caa ctt cag cta cag tgt tag                                          21

<210> SEQ ID NO 13
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 13 tta tac aac aga tgt att cgg t                                        22

<210> SEQ ID NO 14
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 14 aac tgt ctc aaa caa cag atg                                          21

<210> SEQ ID NO 15
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 15 ccg ctc gag aac gca caa tgg aca gcc ctg                              30

<210> SEQ ID NO 16
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 16 ccg ctc gag tac aga gtt tgg aag tga ggg                              30
```